United States Patent [19]

McKeown et al.

[11] Patent Number: 5,792,860
[45] Date of Patent: Aug. 11, 1998

[54] SUBSTITUTED PHTHALOCYANIDES WITH SULFONYL SUBSTITUTED WITH AMINO OR CARBOXYL GROUPS

[75] Inventors: Neil Bruce McKeown; Kevin Edward Treacher; Guy James Clarkson. all of Manchester, United Kingdom

[73] Assignee: The Secretary of State for Defence in Her Majesty's Government of the United Kingdom of Great Britain and Northern Ireland of Defence Evaulation Research Agency. United Kingdom

[21] Appl. No.: 700,405

[22] PCT Filed: Mar. 23, 1995

[86] PCT No.: PCT/GB95/00647

§ 371 Date: Sep. 25, 1996

§ 102(e) Date: Sep. 25, 1996

[87] PCT Pub. No.: WO95/26381

PCT Pub. Date: Oct. 5, 1995

[30] Foreign Application Priority Data

Mar. 25, 1994 [GB] United Kingdom ............ 9405970

[51] Int. Cl.$^6$ ............... C07D 478/22; C09B 47/00
[52] U.S. Cl. ............... 540/140; 540/128; 540/122; 540/139; 359/103
[58] Field of Search ............... 540/122, 128, 540/139, 140; 359/103; 430/270

[56] References Cited

U.S. PATENT DOCUMENTS

| 5,348,840 | 9/1994 | Sakamoto et al. ............ 430/270 |
| 5,506,708 | 4/1996 | Harrison et al. ............ 359/103 |

FOREIGN PATENT DOCUMENTS

| 0232427A1 | 8/1986 | European Pat. Off. . |
| 0373643 | 12/1989 | European Pat. Off. . |
| 0433220A2 | 11/1990 | European Pat. Off. . |
| 0519423A2 | 6/1992 | European Pat. Off. . |
| 0558449A1 | 2/1993 | European Pat. Off. . |
| 2200650 | 6/1987 | United Kingdom . |
| WO87/01076 | 2/1987 | WIPO . |

Primary Examiner—Mukund J. Shah
Assistant Examiner—Pavanaram K. Sripada
Attorney, Agent, or Firm—Nixon & Vanderhye

[57] ABSTRACT

Phthalocyanines of formula (I) are described, wherein M is a metal atom, metal compound or silicon or a compound of silicon or is 2H; $R_1$–$R_{25}$ may be the same or different, provided that at least one of $R_1$–$R_{25}$ has the Formula (II), wherein Y groups are independently H, $C_{1-3}$ alkyl, halogen or CN; k=0 or 1; l=1–10; m=0 or 1; n=1–10; p=1–10; q=1–20; r=0 or 1; X may be H, Me, etc ... Compounds of the above formulae are useful in a broad range of applications, including electrooptical devices, and for use in optical recording media.

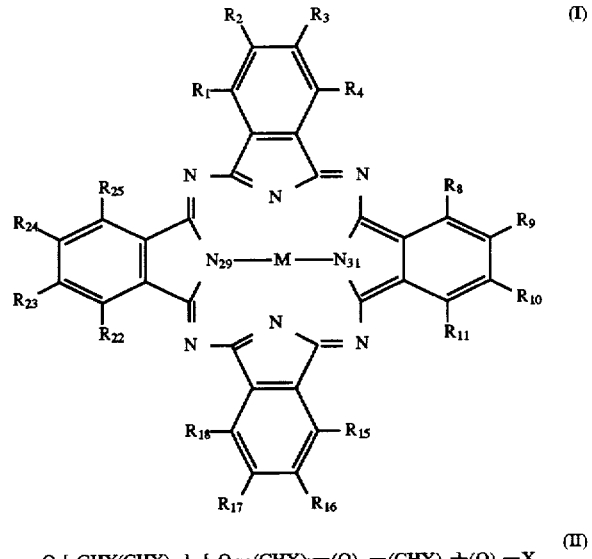

17 Claims, 4 Drawing Sheets

→ Pc series 1

Pc series 4

(wherein R is H, methyl or trityl)

SUBSTITUTED PHTHALOCYANIDES WITH SULFONYL SUBSTITUTED WITH AMINO OR CARBOXYL GROUPS

This is a 35 U.S.C. 371 of PCT/GB95/00647 filed Mar. 23, 1995.

This invention relates to novel substituted phthalocyanines and to certain uses thereof.

Phthalocyanine has the following formula:

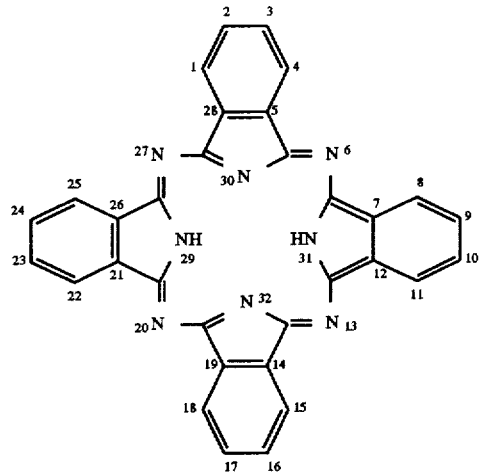

The nomenclature for the numbering of the Benzo portion is also included in the above depiction. Generally substituents in the $R_{2,3,9,10,16,17,23,24}$ positions are referred to as peripheral groups and substituents in the $R_{1,4,8,11,15,18,22,25}$ positions are referred to as non-peripheral groups.

It is known that some phthalocyanine compounds exhibit liquid crystalline behaviour.

The majority of known liquid crystalline compounds have a generally rod-shaped molecular structure and are often characterised by nematic and/or smectic mesophases. There are, however, a number of known compounds which are characterised by a generally disc-like molecular structure. These compounds are termed discotic compounds, which can be characterised by discotic nematic or columnar mesophase(s).

Discotic compounds can be based on a number of "cores", eg benzene, truxene, metallophthalocyanine, phthalocyanines and triphenylene.

Guillon et al Mol. Cryst. Liq. Cryst.; 1985, vol 130, pp223–229, discuss columnar mesophases from metallated and metal free derivatives of phthalocyanine in which the phthalocyanine is substituted on the benzene rings with various groups all of which are attached to the phthalocyanine core via a $CH_2$ unit.

Piechocki and Simon; New Journal of Chemistry, vol 9, no 3, 1985, p159–166, report the synthesis of octa-substituted phthalocyanine derivatives forming discotic mesophases. The side chains are linked to the phthalocyanine core via a $CH_2$ unit.

Most liquid crystal compounds are known as thermotropic liquid crystal compounds. Thermotropic liquid crystals exist in dependence of the temperature in certain temperature intervals. In some cases when different substances are mixed together the mixture can exhibit different phases not only as the temperature is changed, but also as the concentration of one component of the mixture is changed. When the liquid crystal phase is dependent on the concentration of one component in another it is called a lyotropic liquid crystal. The easiest way to make a lyotropic liquid crystal mixture is to start with a molecule that possesses end groups with different properties. For example one end could show an affinity for water and the other end tends to exclude water. Molecules which possess both a hydrophilic group and a part which is a hydrophobic group can display characteristics of both classes, therefore they are called amphiphilic molecules.

Lyotropic liquid crystals have numerous potential applications including detergents, the recovery of oil from porous rocks and in the food industry for example as food emulsifiers. There may also be medical applications for lyotropic liquid crystal systems. For example, amphiphilic materials could help to make drugs more soluble in the blood.

For a review of phthalocyanine thermotropics, see Simon and Bassoul in Phthalocyanines, Properties and Applications, Ed., C. C. Leznoff and A. B. P. Lever. V.C.H. Publishers 1992, p 227.

Some phthalocyanines also absorb radiation in the far-red to near infra-red regions of the electromagnetic spectrum. Compounds which absorb strongly at wavelengths of laser light can in principle be exploited as guest dyes dissolved in liquid crystalline host materials in a laser addressed system.

Materials have been proposed for laser addressed applications in which laser beams are used to scan across the surface of the material or leave a written impression thereon. For various reasons, many of these materials have consisted of organic materials which are at least partially transparent in the visible region. The technique relies upon localised absorption of laser energy which causes localised heating and in turn alters the optical properties of the otherwise transparent material in the region of contact with the laser beam. Thus as the beam traverses the material, a written impression of its path is left behind. One of the most important of these applications is in laser addressed optical storage devices, and in laser addressed protection displays in which light is directed through a cell containing the material and is projected onto a screen. Such devices have been described by Khan Appl. Phys. Lett. Vol. 22, p 111, 1973; and by Harold and Steele in Proceedings of Euro display 84, pages 29–31, September 1984, Paris, France, in which the material in the device was a smectic liquid crystal material. Devices which use a liquid crystal material as the optical storage medium are an important class of such devices. The use of semiconductor lasers, especially $Ga_xAl_{1-x}As$ lasers where x is from 0 to 1, and is preferably 1, has proven popular in the above applications because they can provide laser energy at a range of wavelengths in the near infra-red which cannot be seen and thus cannot interfere with the visual display, and yet can provide a useful source of well-defined, intense heat energy. Gallium arsenide lasers provide laser light at wavelengths of about 850 nm, and are useful for the above applications. With increasing Al content (x<1), the laser wavelength may be reduced down to about 750 nm.

One of the main problems associated with the use of the above materials is that it has proved difficult to provide materials which are transparent in the visible region and yet are strong absorbers in either the uv or ir region, preferably in the near ir region. The use of dyes within these materials can provide strong absorption at certain wavelengths, but few dyes are transparent in the visible region and many are insoluble in the type of materials used for laser addressed applications. EP-A-0155780 discloses a group of metal and metal-free phthalocyanines which have been used as infrared absorbing dyes for a number of applications. These phthalocyanines contain from 5 to 16 peripheral organic substituent groups that are linked to the phthalocyanine through sulphur, selenium, tellurium or nitrogen atoms. However, very few of the groups disclosed absorb infra-red radiation strongly at or near the wavelength of a gallium arsenide laser (850 nm). This problem also applies to a further group of infra-red absorbing phthalocyanines disclosed in EP-A-0134518. This further group consists of naphthalocyanines which are peripherally substituted with alkyl groups and centrally substituted with a metal atom or a chloride, bromide or oxide thereof. Materials Science II/1-2, 1976 pages 39–45 discloses the synthesis of octamethoxyphthalocyanines but these are insoluble in organic solvents and as such are unsuitable for acting as dyes in liquid crystalline solvents for laser addressed systems.

UK Patent GB 2,229,190 B relates to certain novel substituted phthalocyanines, methods for their preparation and to certain uses thereof. For example the compounds described in GB 2,229,190 B are suitable for use in optical recording media. Kuder in J. of Imaging Science, vol 32, (1988), p51–56 discusses how phthalocyanine dyes may be used in laser addressed optical recording media; in particular it sets out how active layers may be deposited.

A number of phthalocyanine (Pc) derivatives have been proposed as potential photodynamic therapeutic (PDT) agents. The combination of a sensitizer and electromagnetic radiation for the treatment of cancer is commonly known as photodynamic therapy. In the photodynamic therapy of cancer, dye compounds are administered to a tumour-bearing subject. These dye substances may be taken up, to a certain extent, by the tumour. Upon selective irradiation with an appropriate light source the tumour tissue is destroyed via the dye mediated photo-generation of species such as singlet oxygen or other cytotoxic species such as free radicals, for example hydroxy or superoxide. Most biological studies on Pc compounds related to PDT have been conducted with water soluble sulfonated metallophthalocyanines as described by I. Rosenthal, *Photochem. Photobiol.* 53(6), 859–870, 1991. Methods for synthesizing these compounds often results in mixtures of compounds containing a variety of isomers and/or different degrees of sulfonation.

UK patent application 9317881.2 describes substituted metallophthalocyanines and phthalocyanines as PDT agents.

Patent WO 93/09124 describes the use of water soluble salt or acid forms of transition metal phthalocyanines for use in photodynamic therapy. In this patent application, phthalocyanines containing second or third row transition metals with a $d^6$ low-spin electronic configuration are disclosed. The compounds exemplified in patent application WO 93/09124 contain Ru.

Phthalocyanine derivatives have also been used in Langmuir Blodgett films as described in UK patent 2,229,190 B.

According to this invention there is provided phthalocyanine (Pc) compounds of general Formula I:

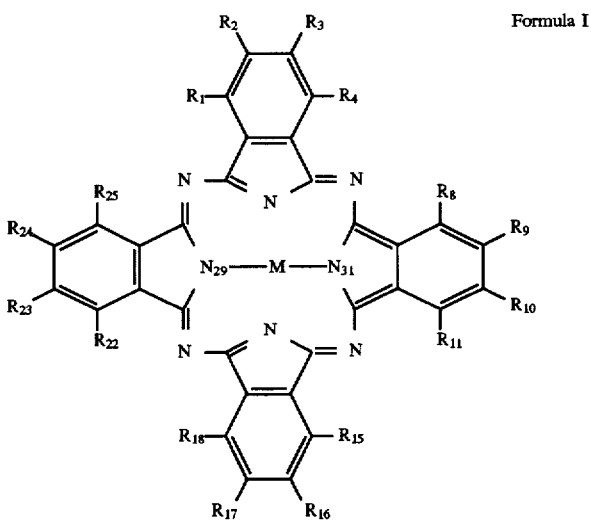

Formula I wherein

M is a metal atom, metal compound or silicon or a compound of silicon or is 2H; one H being bonded to each of the two nitrogen atoms depicted as being bonded to M (positions 29 and 31 shown);

$R_1$–$R_{25}$ may be the same or different provided that at least one of $R_1$–$R_{25}$ has the following Formula II:

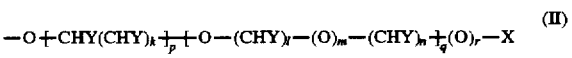

(II)

wherein Y groups are independently H, $C_{1-3}$ alkyl, halogen or CN;

k=0 or 1; l=1–10; m=0 or 1; n=1–10; p=1–10; q=1–20; r=0 or 1;

X may be one or more of the following groups:
H, Me, cholesteryl, OH, COR or COOR where R is straight or branched chain alkyl, or X may be described by the following formula:

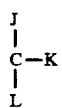

wherein C is carbon and J,K,L may be, independently of each other:

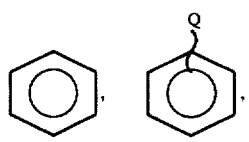

wherein Q indicates that the phenyl ring may independently carry one or more substituents including straight or branched chain alkyl or alkoxy, halogen, CN, OH, H;

For the cases wherein not all of $R_1$–$R_{25}$ are given by formula II then those $R_1$–$R_{25}$ groups not described by formula II may be independently any of the following groups which are referred to as R":

straight or branched chain alkyl or alkoxy, H, alkene, cholesteryl, trityl.

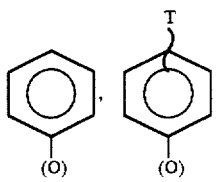

wherein (O) indicates an oxygen may or may not be present; T indicates that the phenyl or phenoxy ring may be substituted with one or more substituents selected from straight or branched chain alkyl or alkoxy, halogen, CN, OH, H; preferably:

$R_{1,4,8,11,15,18,22,25}=H$;

all Y groups=H; k=1; p=1; l=1; m=0; n=1; q=2–20; r=1 and X is chosen from one of the following groups:

Me, trityl, H;
R"=straight chain alkyl or alkoxy containing up to 20 carbon atoms;
tert-butyl;
di-(tert-butyl)-phenoxy;
cholesteryl.

The metal atom may be present for example as the metal with an oxidation state of +2 or it may be present with other ligands (or anions) attached to it. These ligands (or anions) may serve the purpose of altering the hydrophobicity of the molecule as a whole. Examples of suitable anions include chloride, bromide or oxide. Examples of suitable metals include Ni, Pb, V, Pd, Co, Nb, Al, Sn, Zn, Cu, Mg, Ca, In, Ga, Fe, Eu, Lu and Ge. Preferably when M is a metal or metal compound then the metal is, or the metal compound contains Cu, Zn, Pb, V, Co, Eu, Lu. Examples of suitable metal compounds include VO.

The compounds described by the current invention are useful for a broad range of applications.

Many of the compounds described by formula I show liquid crystalline behaviour and are thus usefully employed in liquid crystal devices. The compounds of formula I may also be included in a mixture, where the mixture comprises at least two compounds. Typical mixtures include mixtures consisting of compounds of Formula I, and also mixtures comprising at least one compound of Formula I and at least one compound not of Formula I. Donor/acceptor mixtures, and mixtures having lower melting points than melting points of individual compounds, are desirable for obtaining room temperature liquid crystal phases in discotic liquid crystal materials and for control of phase sequence and transition temperatures.

A further aspect of the invention includes use of the compounds of Formula I, and use of mixtures including Formula I, in a liquid crystal device. Typically such devices include linear and non-linear electrical, optical and electro-optical devices, magneto-optical devices, and devices providing responses to stimuli such as temperature changes and total or partial pressure changes.

Many of the compounds described by the present invention also exhibit lyotropic behaviour and may therefore be useful as detergents, recovering oil from porous rocks, in the food industry, providing they are sufficiently non-toxic, for example as emulsifiers. They may also have useful applications in the medical field as detailed earlier.

Polyethylene oxides can complex alkali metal ions, for example $Li^+$ and have been used as polyelectrolytes in solid state battery applications, see Charadame in 'Macromolecules', ed. Benoit and Rempp, Pergamon press, New York, 1982, p226. The compounds of the invention may also be useful as polyelectrolytes, they are able to stabilise charge, therefore there exist a number of applications within battery technology.

The compounds of the present invention are suitable for use in optical recording media. Typically the phthalocyanine will absorb in the near-infrared. In order to make an optical recording media using a near-infrared absorber, the near-infrared absorber may be coated or vacuum-deposited onto a transparent substrate. European patent application EP 0 337 209 A2 describes the processes by which the above optical-recording media may be made. Further the materials described in EP 0 337 209 A2 are useful in near-infrared absorption filters and liquid crystal display devices, as are the compounds described by the current invention. As described in EP 0 337 209 A2, display materials can be made by mixing a near-infrared absorber of formula I with liquid crystal materials such as nematic liquid crystals, smectic liquid crystals and cholesteric liquid crystals. The compounds of the current invention may be incorporated into liquid crystal panels wherein the near-infrared absorber is incorporated with the liquid crystal and a laser beam is used to write an image. Mixtures of phthalocyanines of the current invention may be mixed with liquid crystal materials in order to be used in guest-host systems. GB 2,229,190 B describes the use of phthalocyanines incorporated into liquid crystal materials and their subsequent use in electro-optical devices.

The materials of the current invention may also be incorporated in Langmuir-Blodgett (LB) films. LB films incorporating phthalocyanines of the current invention may be laid down by conventional and well known techniques, see R. H. Tredgold in 'Order in Thin Organic Films', Cambridge University Press, p74, 1994 and references therein. Generally an LB film is prepared by depositing a monolayer of a surface-active material onto a water surface; this may be done using well established techniques. The molecules of the surface active material align in the monolayer, the hydrophilic ends remaining in the water, and the hydrophobic end projecting out of the surface. By other known techniques this monolayer may be transferred essentially intact onto the surface of a solid substrate and further monolayers deposited on the layer on the substrate to form a film, ie an LB film.

It may be advantageous to polymerise certain of the compounds described by the current invention. Polymerised phthalocyanines may be used in, for example, LB films. There are numerous ways by which the phthalocyanine compound may be polymerised. Polymerisation may be effected via one or more of the positions $R_1-R_{25}$ as described in formula I of the current invention or via the central metal atom or metal compound, or polymerisation may be realised by a combination of the above methods. An example of a suitable phthalocyanine substituent which may used to effect polymerisation is an unsaturated substituent such as an alkene group.

Main chain or side chain liquid crystal polymers may also be made using the compounds of the present invention, or metal—metal linked liquid crystal polymers.

LB films including compounds of the current invention may be used as optical or thermally addressable storage media.

The compounds of the current invention may also be used as molecular wires, see R. J. M. Nolte et al, Angew. Chem. Int. Ed. Eng., vol 33, part 21, page 2173, 1994.

It is known that some phthalocyanines are excellent generators of third order non-linear optical effects and thus show promise for use in photonic devices including all-optical switches and computers, see Bredas, Adant, Tackx Persoons and Pierce, Chem. Rev., 94, p243, 1994. The materials of the present invention may show such effects and be used in such devices.

The invention will now be described, by way of example only, with reference to the following diagrams.

Figure 1:
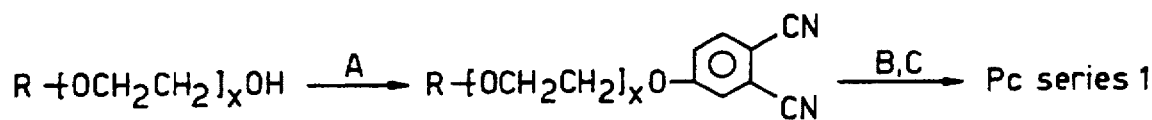
FIGS. 1–5 show synthetic schemes for the preparation of compounds highlighted in Series 1–5.

Reagents used in the synthetic route of FIG. 1 are:
A: 4-nitrophthalonitrile, DMF, anhydrous $K_2CO_3$, rt, 5 days
B: $LiOC_5H_{11}$—$C_5H_{11}OH$, 135° C., 2h
C: AcOH, 0.5h
where:
DMF=dimethylformamide
rt=room temperature 4-Nitrophthalonitrile = 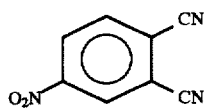

Figure 2:
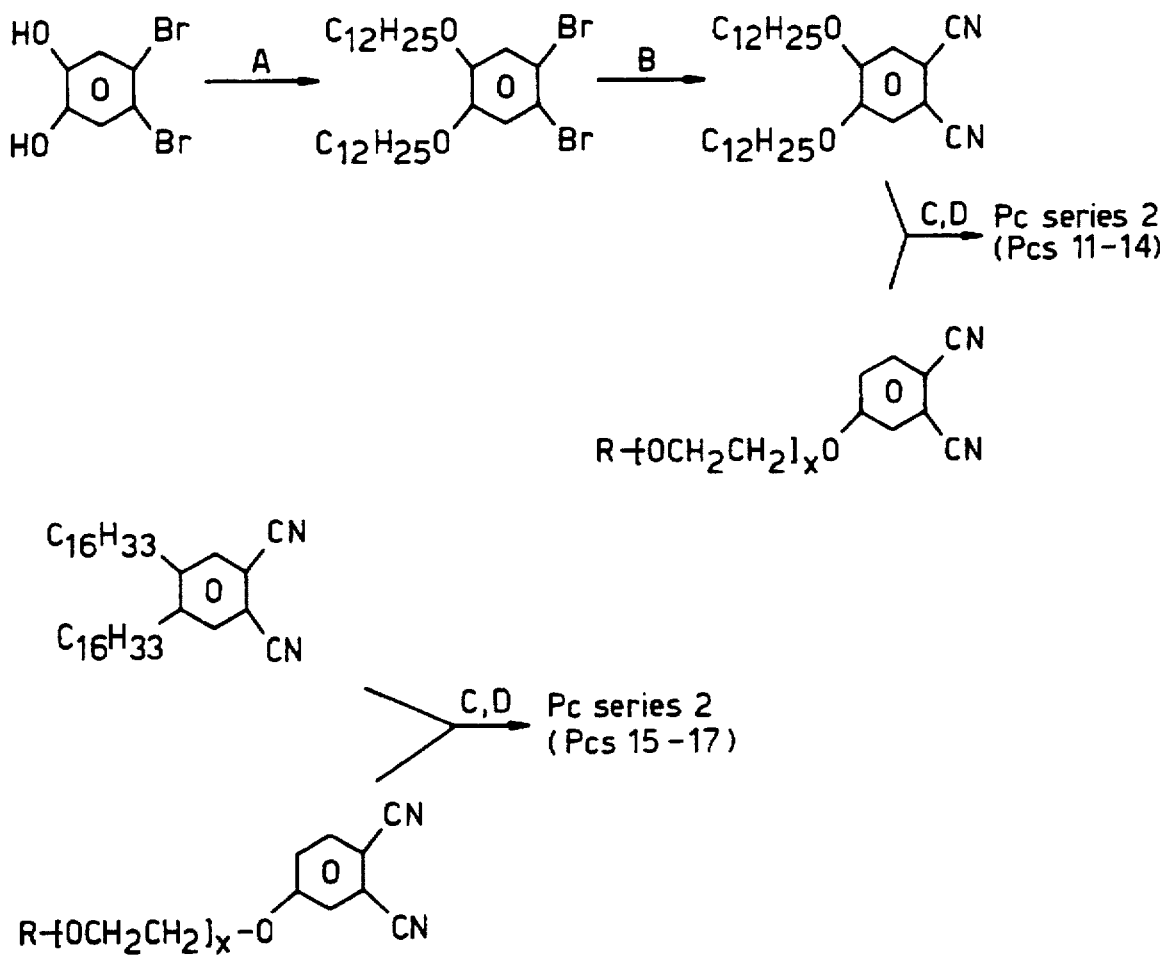

Reagents used in the synthetic route of FIG. 2 are:
A: $C_{12}H_{25}Br$, butanone, $K_2CO_3$, 24h
B: CuCN, DMF, 150° C., 5h
C: $LiOC_5H_{11}$—$C_5H_{11}OH$, 135° C. 2h
D: AcOH, 0.5h
Pc mixtures separated by chromatography.

Figure 3:
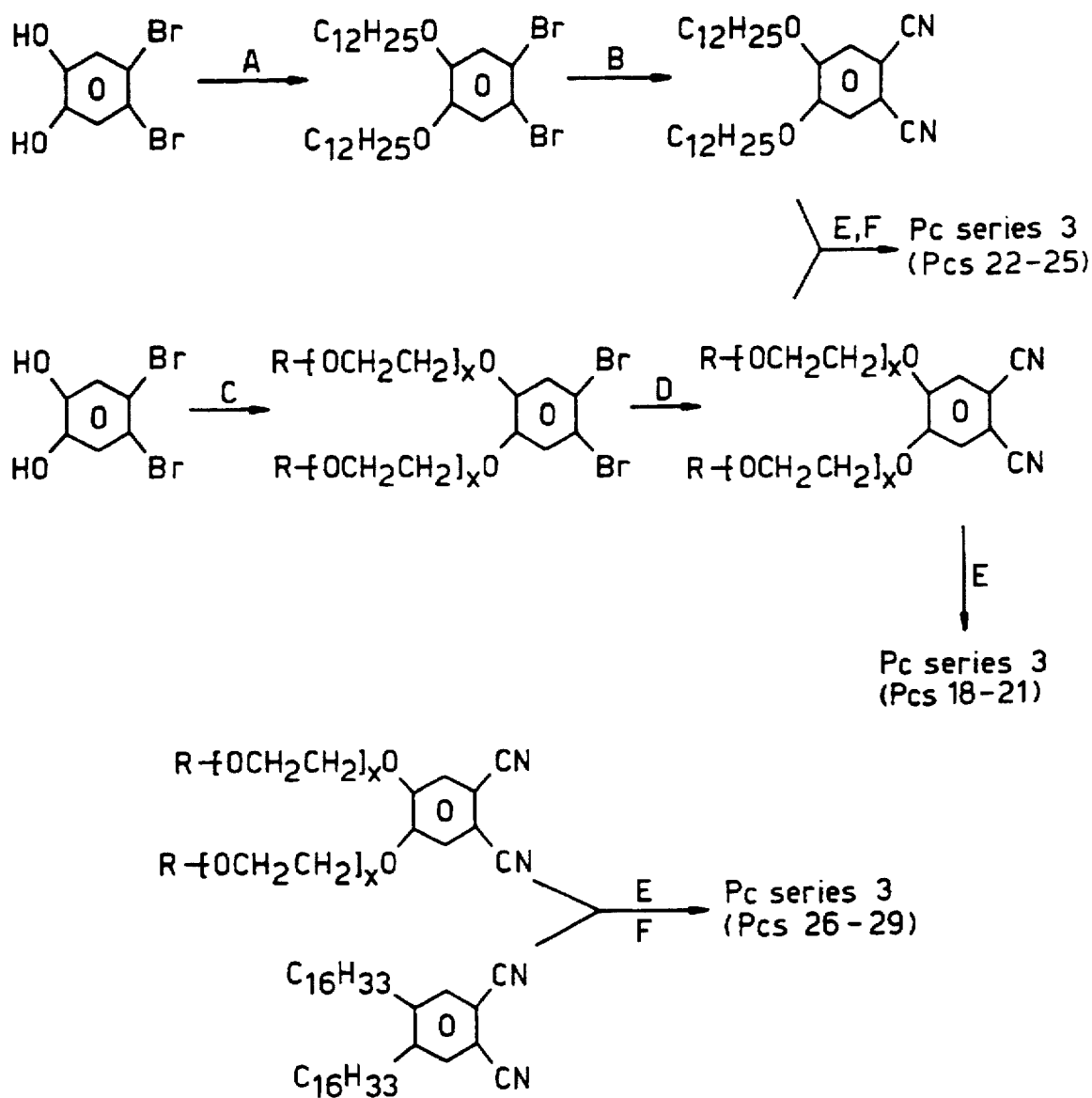

Reagents used in the synthetic route of FIG. 3 are:
A: $C_{12}H_{25}Br$, butanone, $K_2CO_3$, 24h
B: CuCN, DMF, 150° C., 5h
C: R—$[OCH_2CH_2]_xO$-Tos, butanone, $K_2CO_3$, 24h
D: CuCN, DMF, 150° C., 5h
E: for Pcs 19–25; $NH_3$, $NaOCH_3$, 2-dimethylaminoethanol
E: for Pcs 18, 26–29, $LiO(CH_2CH_2O)_3CH_3$, $HO(CH_2CH_2O)_3CH_3$, 150° C.
F: for Pcs 18, 26–29; AcOH, 0.5h
wherein Tos=tosylate.
Pc mixtures separated by chromatography.

Figure 4:
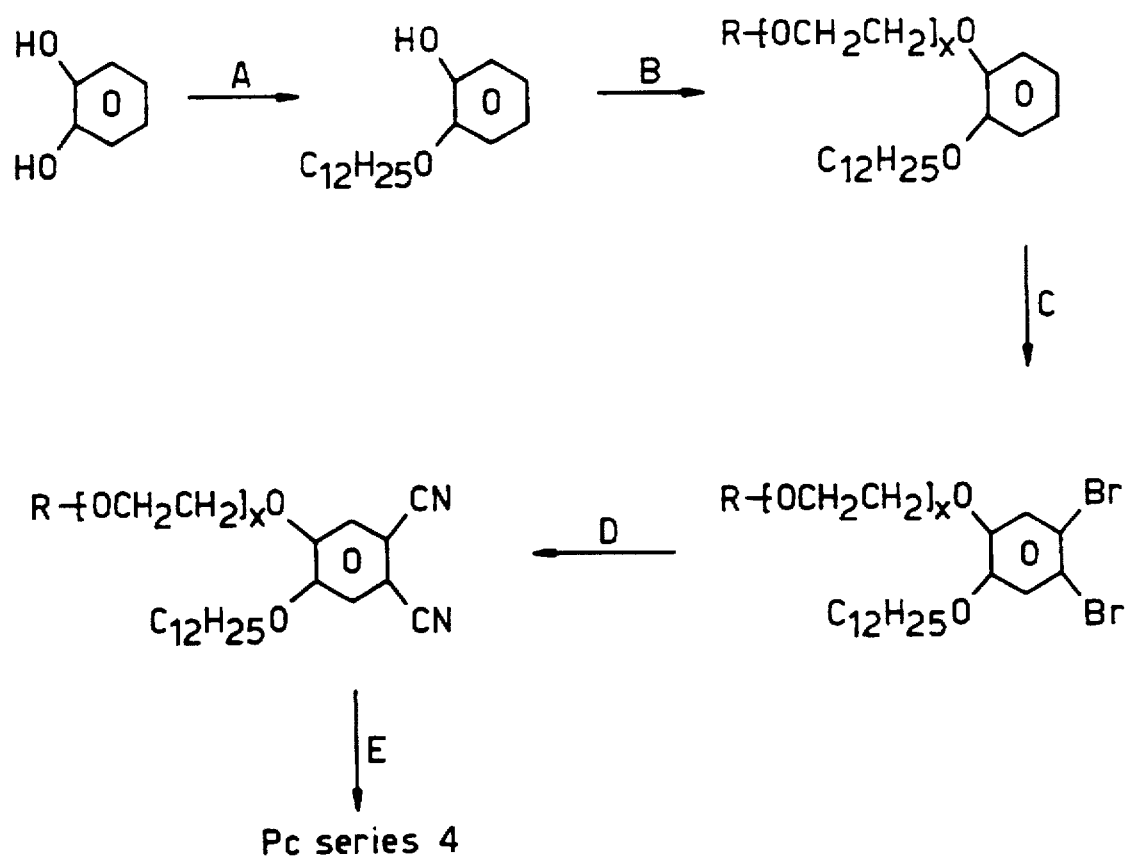
Figure 5:
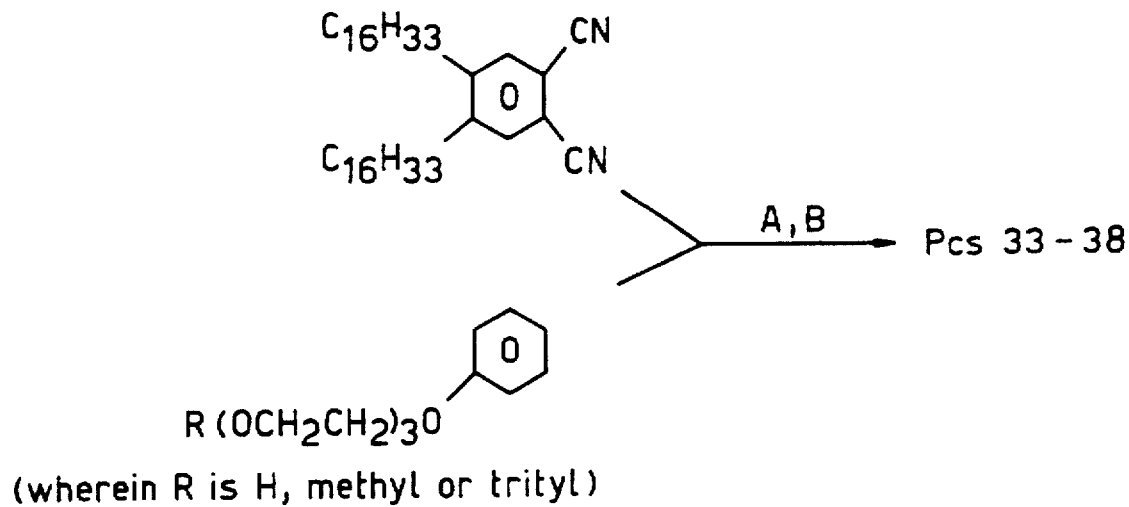
Figure 5:
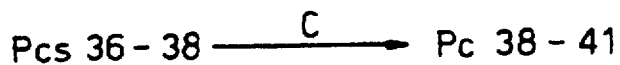
Figure 6:
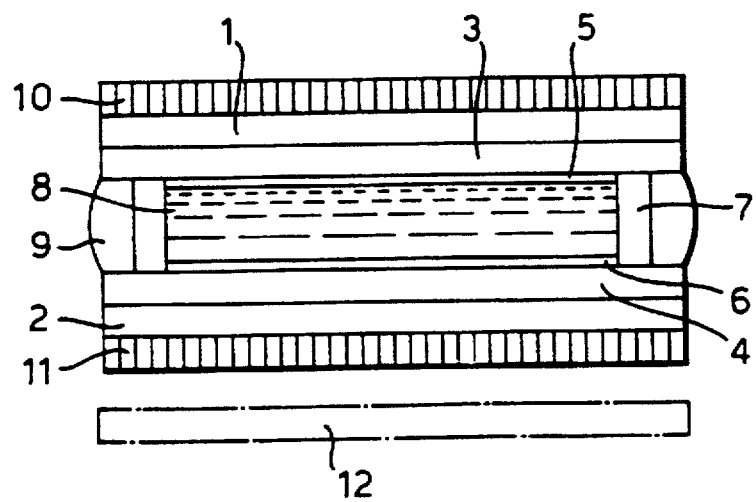
FIG. 6 illustrates a liquid crystal device.

Reagents used in the synthetic route of FIG. 4 are:
A: $C_{12}H_{25}Br$, butanone, $K_2CO_3$, 100° C., 24h
B: R—$[OCH_2CH_2]_xO$-Tos, butanone, $K_2CO_3$, 24h
C: $Br_2$, $CH_2Cl_2$, 2h, rt
D: CuCN, DMF, 150° C., 5h
E: $NH_3$, $NaOCH_3$, 2-dimethylaminoethanol Reagents used in the synthetic route of FIG. 5 are:
A: $LiOC_5H_{11}$, $C_5H_{11}OH$, 135° C.
B: AcOH, 30 min
C: HCl, THF, 1h An example of the use of a compound of Formula I in a liquid crystal material and device embodying the present invention will now be described with reference to FIG. 6.

The liquid crystal device consists of two transparent plates, 1 and 2, in this case made from glass. These plates are coated on their internal face with transparent conducting electrodes 3 and 4. An alignment layer 5,6 is introduced onto the internal faces of the cell so that a planar orientation of the molecules making up the liquid crystalline material will be approximately parallel or at a small angle to the glass plates 1 and 2. For some types of display the plane of the molecules is approximately perpendicular to that of the glass plates, and at each glass plate the alignment directions are orthogonal. The electrodes 3, 4 may be formed into row and column electrodes so that the intersections between each column and row form an x, y matrix of addressable elements or pixels. A spacer 7 eg of polymethyl methacrylate separates the glass plates 1 and 2 to a suitable distance eg 2 microns. Liquid crystal material 8 is introduced between glass plates 1, 2 by filling the space in between them. The spacer 7 is sealed with an adhesive 9 in a vacuum using an existing technique. Polarisers 10, 11 are arranged in front of and behind the cell. For some devices, only one or even no polarisers are required.

The device may operate in a transmissive or reflective mode. In the former, light passing through the device, eg from a tungsten bulb, is selectively transmitted or blocked to form the desired display. In the reflective mode a mirror (12) is placed behind the second polariser 11 to reflect ambient light back through the cell and two polarisers. By making the mirror partly reflecting the device may be operated both in a transmissive and reflective mode.

The alignment layers 5,6 have two functions one to align contacting liquid crystals molecules in a preferred direction and the other to give a tilt to these molecules—a so called surface tilt—of a few degrees typically around 4° or 5°. The alignment layers 5, 6 may be formed by placing a few drops of the polyimide onto the cell wall and spinning the wall until a uniform thickness is obtained. The polyimide is then cured by heating to a predetermined temperature for a predetermined time followed by unidirectional rubbing with a roller coated with a nylon cloth.

In another example a layer of liquid crystal material is exposed to a gas to provide a gas sensor.

The following compounds are example compounds that have been synthesised for the present invention.

Series 1: Tetra-substituted phthalocyanines

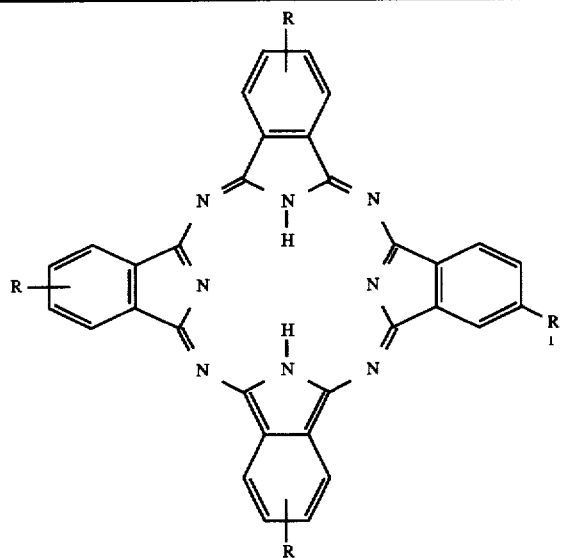

|  | Mesophase properties/°C. | |
|---|---|---|
|  | Thermotropic | Lyotropic |
| 1. R = ₁R = CH₃—(OCH₂CH₂)₃—O— | 78->330 (D$_{ho}$) | N$_c$ & D$_{ho}$ |
| 2. R = ₁R = CH₃—(OCH₂CH₂)₈—O— | 11–180 (D$_{ho}$) | N$_c$ & D$_{ho}$ |
| 3. R = ₁R = CH₃—(OCH₂CH₂)₁₂—O— | none | D$_{ho}$ (water) |
| 4. R = ₁R = CH₃—(OCH₂CH₂)₁₆—O— | none | D$_{ho}$ (water) |
| 5. R = ₁R = Trityl—(OCH₂CH₂)₃—O— | 60–280 (D$_{hd}$) | none |
| 6. R = ₁R = Trityl—(OCH₂CH₂)₄—O— | 28–222 (D$_{hd}$) | none |

|  | Thermotropic |
|---|---|
| 7. R = CH₃—(OCH₂CH₂)₃—O—, ₁R = Di-(tert-butyl)-phenoxy- | 60–300 (D$_{ho}$) |
| 8. R = CH₃—(OCH₂CH₂)₃—O—, ₁R = tert-butyl | 70–300 (D$_{ho}$) |
| 9. R = CH₃—(OCH₂CH₂)₃—O—, ₁R = cholesteryl | 90–125 (D$_{ho}$) |
| 10. R = ₁R = H—(OCH₂CH₂)₃—O— | 86->320 (D$_{ho}$) (+N$_c$ and D$_{ho}$ lyotropic phases in ethanol) | wherein:
trityl is

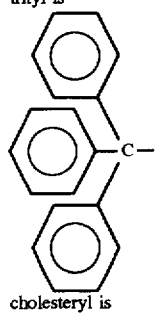

cholesteryl is

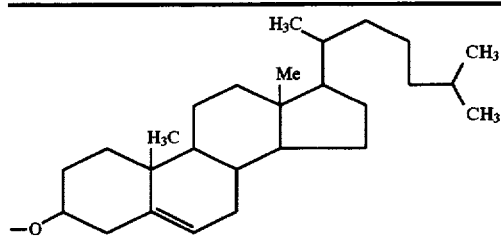

10. is made from Pc 5 by acid catalysed hydrolysis of the trityl groups.

Unsymmetrical compounds 6,7,8 were made by mixed phthalonitrile reactions between 9 equivalents of:

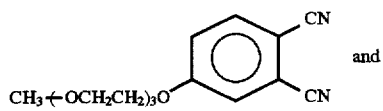 and

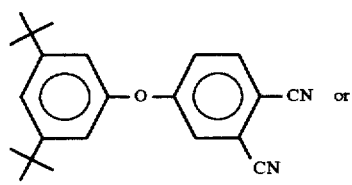 or

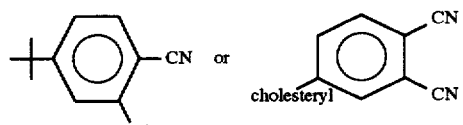 or

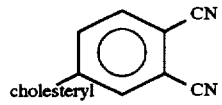

was made as depicted in FIG. 1 Scheme 1 except the starting material was cholesterol.

This compound was separated from the symmetrical Pc(1) by column chromatography.

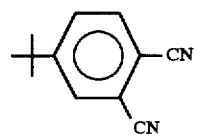

is commercially available from TCI Chemicals (Tokyo)

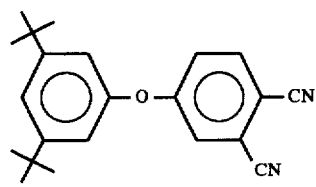

was made as below:

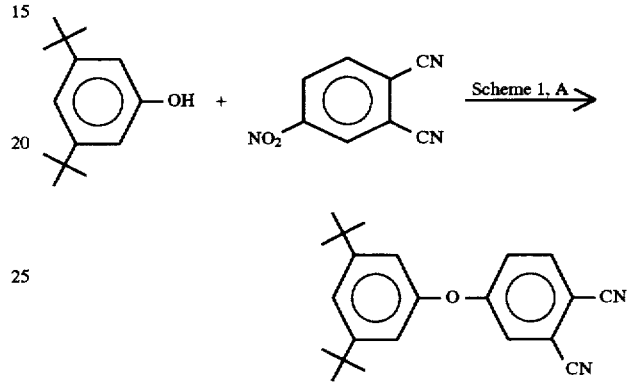

Series 2: Hepta-substituted phthalocyanines

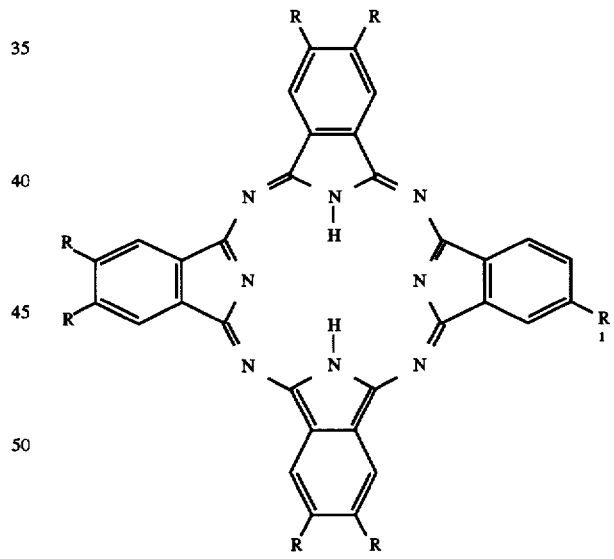

|  | Mesophase properties/°C. |
|---|---|
| 11. R = $C_{12}H_{25}O$ — $_1R$ = $CH_3$ ($OCH_2CH_2)_3$ — O — | 72–320 ($D_{ho}$) |
| 12. R = $C_{12}H_{25}O$ — $_1R$ = $CH_3$ ($OCH_2CH_2)_8$ — O — | 57–290 ($D_{ho}$) |
| 13. R = $C_{12}H_{25}O$ — $_1R$ = $CH_3$ ($OCH_2CH_2)_{12}$ — O — | 45–240 ($D_{ho}$) |
| 14. R = $C_{12}H_{25}O$ — $_1R$ = Trityl ($OCH_2CH_2)_3$ — O — | 45–297 ($D_{ho}$) |

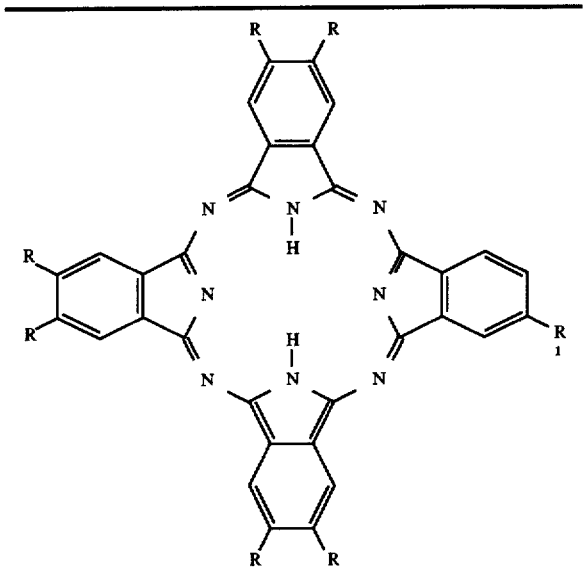

| | Mesophase properties/°C |
|---|---|
| 15. R = $C_{16}H_{33}$ — $_1$R = $CH_3$ ($OCH_2CH_2)_3$ — O — | 85–130 ($D_{rd}$), 130–204 ($D_{hd}$) |
| 16. R = $C_{16}H_{33}$ — $_1$R = Trityl ($OCH_2CH_2)_4$ — O — | 86–166 ($D_{hd}$) |
| 17. R = $C_{16}H_{33}$ — $_1$R = H ($OCH_2CH_2)_4$ — O — | 81–107 ($D_{rd}$), 107–190 ($D_{hd}$) |

Phthalocyanine 13 was made from a mixed phalonitrile reaction between

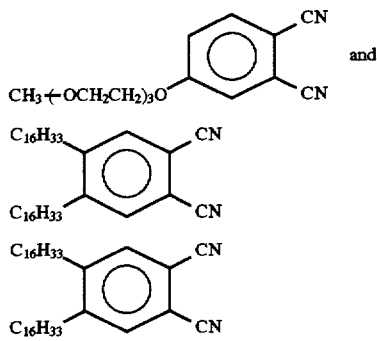

was made according to the method described by Ohta, Jacquemin, Sirlin, Bosio and Simon in New Journal of Chemistry, 1988, 12, p751 and is represented below:

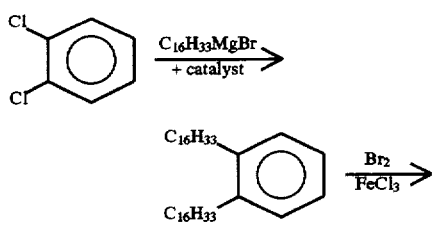

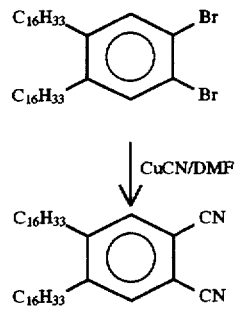

Pc 17 was made by acid catalysed hydrolysis of Pc 16.

Series 3: Octa-substituted phthalocyanines

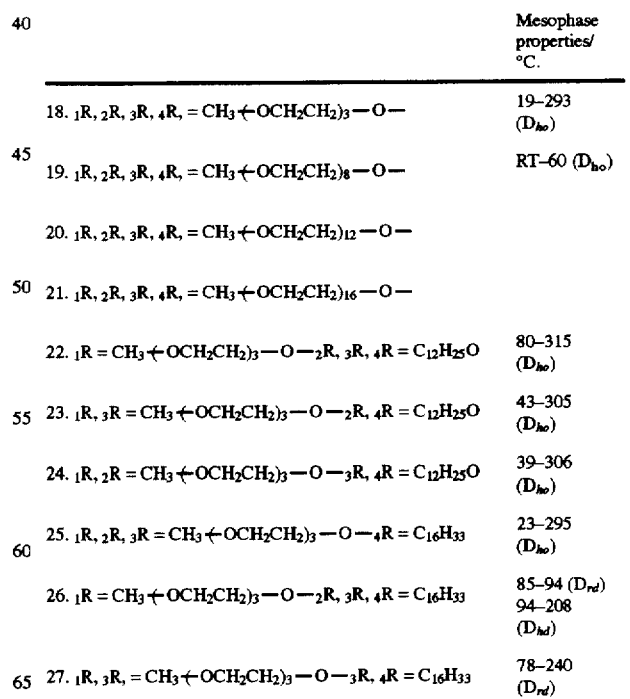

| | Mesophase properties/°C |
|---|---|
| 18. $_1$R, $_2$R, $_3$R, $_4$R, = $CH_3$ ($OCH_2CH_2)_3$ — O — | 19–293 ($D_{ho}$) |
| 19. $_1$R, $_2$R, $_3$R, $_4$R, = $CH_3$ ($OCH_2CH_2)_8$ — O — | RT–60 ($D_{ho}$) |
| 20. $_1$R, $_2$R, $_3$R, $_4$R, = $CH_3$ ($OCH_2CH_2)_{12}$ — O — | |
| 21. $_1$R, $_2$R, $_3$R, $_4$R, = $CH_3$ ($OCH_2CH_2)_{16}$ — O — | |
| 22. $_1$R = $CH_3$ ($OCH_2CH_2)_3$ — O — $_2$R, $_3$R, $_4$R = $C_{12}H_{25}O$ | 80–315 ($D_{ho}$) |
| 23. $_1$R, $_3$R = $CH_3$ ($OCH_2CH_2)_3$ — O — $_2$R, $_4$R = $C_{12}H_{25}O$ | 43–305 ($D_{ho}$) |
| 24. $_1$R, $_2$R = $CH_3$ ($OCH_2CH_2)_3$ — O — $_3$R, $_4$R = $C_{12}H_{25}O$ | 39–306 ($D_{ho}$) |
| 25. $_1$R, $_2$R, $_3$R = $CH_3$ ($OCH_2CH_2)_3$ — O — $_4$R = $C_{16}H_{33}$ | 23–295 ($D_{ho}$) |
| 26. $_1$R = $CH_3$ ($OCH_2CH_2)_3$ — O — $_2$R, $_3$R, $_4$R = $C_{16}H_{33}$ | 85–94 ($D_{rd}$) 94–208 ($D_{hd}$) |
| 27. $_1$R, $_3$R, = $CH_3$ ($OCH_2CH_2)_3$ — O — $_3$R, $_4$R = $C_{16}H_{33}$ | 78–240 ($D_{rd}$) |

15
-continued

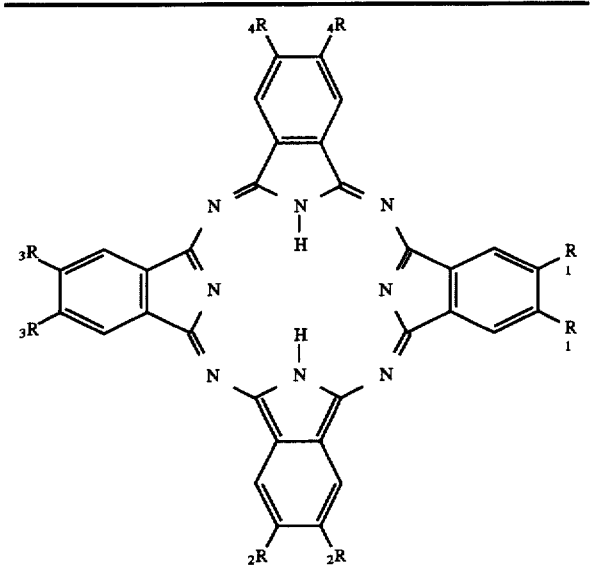

| | Mesophase properties/°C. |
|---|---|
| 28. $_1R, _2R, = CH_3 \{OCH_2CH_2\}_3—O—_3R, _4R = C_{16}H_{33}$ | 78–178 ($D_{rd}$), 178–211 ($D_{hd}$) |
| 29. $_1R, _2R, _3R, = CH_3 \{OCH_2CH_2\}_3—O—_4R = C_{16}H_{33}$ | 43–175 ($D_{rd}$), 175–229 ($D_{hd}$) |
| 30. $_1R, _2R, _3R, _4R, = CH_3 \{OCH_2CH_2\}_8—O—$ Metal ion = $Cu^{2+}$ | RT–85 ($D_{ho}$) |

Phthalocyanine 16 may be prepared by either reaction of the relevant phthalonitriles or isolated from mixed reaction product mixtures.

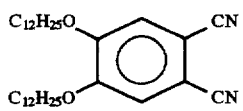

16 was made according to the method described by Ohta, Jacquemin, Sirlin, Bosio and Simon in New Journal of Chemistry, 1988, 12, p751.

Series 4: Octa-substituted phthalocyanines

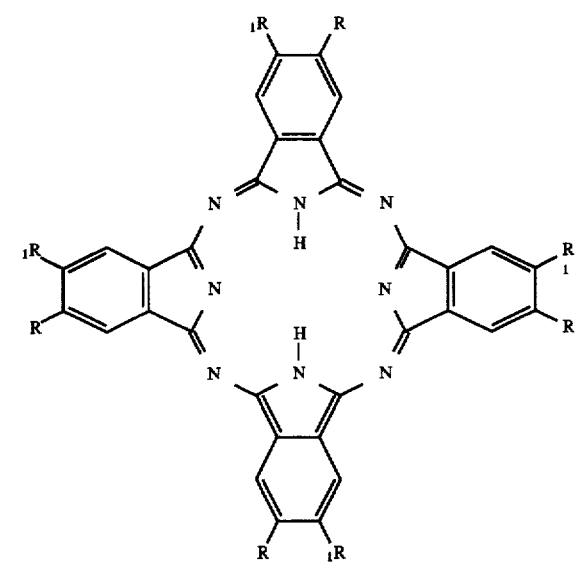

| | Mesophase properties/°C. |
|---|---|
| 31. $R = C_{12}H_{25}O—_1R = CH_3 \{OCH_2CH_2\}_3—O—$ | (12° C.)–307 ($D_{ho}$) |
| 32. $R = C_{12}H_{25}O—_1R = CH_3 \{OCH_2CH_2\}_8—O—$ | RT–95° C. | mixture of isomers

Series 5

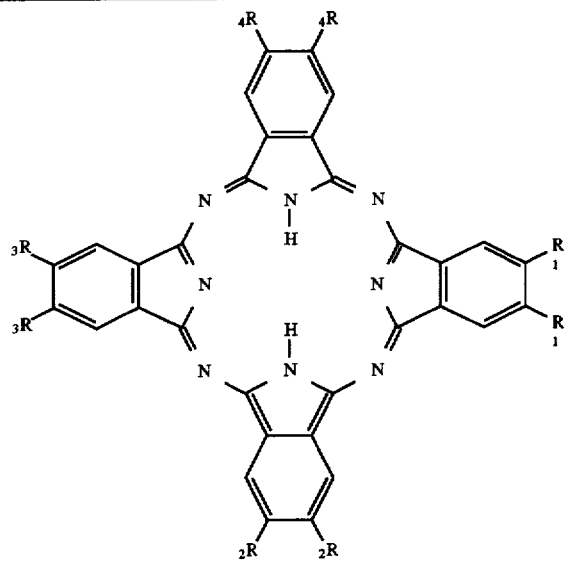

| | Mesophase properties |
|---|---|
| 33. $_1R = {_3}R = C_{16}H_{33} - {_2}R = {_4}R = CH_3(OCH_2CH_2) - O -$ and H | 43–142 (Drd) 142–243 (Dho) |
| 34. $_1R = {_2}R = C_{16}H_{33} - {_3}R = {_4}R = CH_3(OCH_2CH_2) - O -$ and H | 81–92 (Drd) 92–243 (Dho) |
| 35. $_1R = C_{16}H_{33} - {_2}R = {_3}R = {_4}R = CH_3(OCH_2CH_2) - O -$ and H | 102–302 (Dhd) |
| 36. $_1R = {_3}R = C_{16}H_{33} - {_2}R = {_4}R = trityl(OCH_2CH_2) - O -$ and H | 41–191 (Drd) 191–196 (Dhd) |
| 37. $_1R = {_2}R = C_{16}H_{33} - {_3}R = {_4}R = trityl(OCH_2CH_2) - O -$ and H | 77–152 (Dhd) |
| 38. $_1R = C_{16}H_{33} - {_2}R = {_3}R = {_4}R = trityl(OCH_2CH_2) - O -$ and H | 32–177 (Dhd) |
| 39. $_1R = {_3}R = C_{16}H_{33} - {_2}R = {_4}R = H - (OCH_2CH_2) - O -$ and H | 65–217 (Drd) 217–232 (Dhd) |
| 40. $_1R = {_2}R = C_{16}H_{33} - {_3}R = {_4}R = H - (OCH_2CH_2) - O -$ and H | 79–132 (Drd) 132–194 (Dhd) |
| 41. $_1R = C_{16}H_{33} - {_2}R = {_3}R = {_4}R = H - (OCH_2CH_2) - O -$ and H | 45–252 (Drd) 252–272 (Dhd) |

35

SERIES 1

Preparation of metal free tetra(1,4,7,10,13,16,19,22,25-nonaoxahexacosyl) phthalocyanine (2) using the route depicted in FIG. 1

(a) Preparation of 4-(1,4,7,10,13,16,19,22,25-nonaoxahexacosyl)phthalonitrile

A solution of 4-nitrophthalonitrile (2.0 g, 11.5 mmol), polyethylene glycol monomethyl ether (m.w. 350) (5.0 g, 14.3 mmol) and anhydrous potassium carbonate (2 g) in DMF (30 ml) was stirred at 50° C. for three days. Water was added and the mixture extracted with ethyl acetate (5×50 ml). Evaporation of solvent yielded the crude product which was eluted through a silica column (toluene/ethyl acetate) to obtain the desired oligo(ethyleneoxy)-substituted phthalonitriles including 4-((1,4,7,10,13,16,19,22,25-nonaoxahexacosyl) phthalonitrile as a colourless liquid (300 mg, 5%), (Found C, 58.8%; H, 7.5; N, 5.5. $C_{25}H_{38}N_2O_9$ requires C,58.8%; H, 7.5%; N,5.5), $\delta_H$ (200 MHz, solvent $CDCl_3$) 3.3(3H, s), 3.5(2H, t), 3.6(26H, s), 3.8(2H, t), 4.2(2H, t), 7.1–7.7(3H, m). m/e found 510. $C_{23}H_{35}N_2O_9$ requires 510.

Note: all mono-substituted phthalonitrile precursors were prepared using similar methodology.

(b) Preparation of tetra-(1,4,7,10,13,16,19,22,25-nonaoxahexacosyl)phthalocyanine(2)

To a stirred solution of 4-(1,4,7,10,13,16,19,22,25-nonaoxahexacosyl)phthalonitrile (150 mg, 0.29 mmol) in refuxing pentanol was added excess lithium metal. After 2 h the solution was cooled and acetic acid was added (2 ml). The resultant blue mixture was extracted with dichloromethane and dried with anhydrous $MgSO_4$. Evaporation of solvent yielded the crude product which was purified by elution through a silica column (dichloromethane/ethanol) to give tetra-(1,4,7,10,13,16,19,22,25-nonaoxahexacosyl) phthalocyanine (2) (56 mg, 37%), Found: C, 58.45; H, 7.90; N, 5.49; $C_{100}H_{154}N_8O_{36}$ requires C, 58.75 ; H, 7.59; N, 5.48. UV/V is (toluene, $\lambda_{max}$ nm) 702, 666, 641, 606, 394, 340. $\delta_H$ (500 MHz, solvent $C_6H_6$) −3.5(2H, br s) 3.4(12H, s), 3.5 (8H, t), 3.6–4.0 (104H, m), 4.2(8H, m), 4.5(8H, m), 7.6–7.9 (4H, m), 8.4–9.4(8H, m), m/e Found 2044. $^{13}CC_{99}H_{154}N_8O_{36}$ $(M+H)^+$ requires 2044.

The following members of Series 1 were made by similar methods—analytical data is given for each example.

(1): Found: C, 61.95; H, 6.50; N, 9.50; $C_{60}H_{74}N_8O_{16}$ requires: C, 61.95; H, 6.41; N, 9.63. UV/V is (toluene, $\lambda_{max}$ nm) 702, 666, 641, 606, 394, 340. $\delta_H$ (500 MHz, solvent $C_6H_6$) −3.5 (2H, br s), 3.4 (12H, s), 3.45 (8H, t), 3.76 (8H, m), 3.81(8H, m), 3.89 (8H, m), 4.10 (8H, m), 4.40 (8H, m), 7.6–7.9 (4H, m), 8.4–9.4 (8H, m), m/e Found 1163. $C_{60}H_{74}N_8O_{16}$ $(M+H)^+$ requires 1163.

(3) Found: C, 57.8; H, 7.8; N, 4.7; $C_{124}H_{202}N_8O_{48}$ requires: C, 57.88; H, 7.91; N, 4.4. UV/V is (toluene, $\lambda_{max}$ nm) 702, 666, 641, 606, 394, 340. $\delta_H$ (500 MHz, solvent $C_6H_6$) −3.0 (2H, br s), 3.3 (12H, s), 3.6–4.0 (160H, m), 4.2(8H, m), 4.5(8H, m), 7.6–7.9(4H, m), 8.4–9.4(8H, m).

(4): Found: C, 57.01; H, 8.14; N, 3.74; $C_{156}H_{266}N_8O_{64}$ requires: C, 57.16; H, 8.18; N, 3.42. UV/V is (toluene, $\lambda_{max}$ nm) 702, 666, 641, 606, 394, 340. $\delta_H$ (500 MHz, solvent $C_6H_6$) −3.0 (2H, br s), 3.3 (12H, s), 3.6–4.0 (224H, m), 4.2(8H, m), 4.5(8H, m), 7.6–7.9(4H, m), 8.4–9.4(8H, m).

(5): Found: C, 76.25; H, 5.95; N, 5.7; $C_{132}H_{122}N_8O_{16}$ requires: C.76.40; H, 5.92; N, 5.40. UV/V is (toluene, $\lambda_{max}$ nm) 702, 666, 641, 606, 394, 340. $\delta_H$ (500 MHz, solvent $C_6H_6$) −3.4 (2H, br s), 3.45(8H, t), 3.70 (8H, m), 3.81(8H, m), 3.89 (8H, m), 4.10 (8H, m), 4.40 (8H, m), 7.0–9.0(72H, m), m/e Found 2073. $^{13}C_2C_{130}H_{122}N_8O_{16}$ (M+H)$^+$ requires 2073.

(6): Found: C, 74.33; H, 6.12; N, 5.0; $C_{140}H_{138}N_8O_{20}$ requires: C,74.65; H, 6.18; N, 4.97. UV/V is (toluene, $\lambda_{max}$ nm) 702, 666, 641, 606, 394, 340. $\delta_H$ (500 MHz, solvent $C_6H_6$) −3.0 (2H, br s), 3.45(8H, t), 3.70 (8H, m), 3.76 (8H, m), 3.81(8H, m), 3.89 (16H, m), 4.10 (8H, m), 4.40 (8H, m), 7.0–9.0 (72H, m), m/e Found 2254. $^{13}C_2C_{138}H_{138}N_8O_{20}$ (M+H)$^+$ requires 2254.

Phthalocyanines 7–9 were prepared using mixed phthalonitrile reactions as outlined on page 23

(7): Found: C, 66.1; H, 6.9; N, 9.3; $C_{67}H_{80}N_8O_{13}$ requires: C, 66.7; H, 6.9; N, 9.3. UV/V is (toluene, $\lambda_{max}$ nm) 702, 666, 641, 606, 394, 340. $\delta_H$ (500 MHz, solvent $C_6H_6$) −3.5 (2H, br s), 2.5 (18H, s), 3.6 (9H, s), 3.80 (6H, t), 3.90 (6H, m), 3.95 (6H, m), 4.00 (6H, m), 4.2–4.4 (12H, m), 7.0–9.4 (12H, m) m/e Found 1057. $^{13}CC_{66}H_{80}N_8O_{13}$ (M+H)$^+$ requires 1206.

(8): Found: C, 64.5; H, 6.50; N, 10.6; $C_{57}H_{68}N_8O_{12}$ requires: C, 64.75; H, 6.48; N, 10.6. UV/V is (toluene, $\lambda_{max}$ nm) 702, 666, 641, 606, 394, 340. $\delta_H$ (500 MHz, solvent $C_6H_6$) −3.5 (2H, br s), 1.8–2.0 (9H, m), 3.6 (9H, s), 3.80 (6H, t), 3.90 (6H, m), 3.95 (6H, m), 4.00 (6H, m), 4.2–4.4 (12H, m), 7.0–9.4 (12H, m) m/e Found 1057. $C_{57}H_{68}N_8O_{12}$ (M+H)$^+$ requires 1057.

(9): Found: C, 68.8; H, 7.7; N, 8.2; $C_{80}H_{106}N_8O_{13}$ requires: C,69.1; H, 7.7; N, 8.1. UV/V is (toluene, $\lambda_{max}$ nm) 702, 666, 641, 606, 394, 340. $\delta_H$ (500 MHz, solvent $C_6H_6$) −3.5 (2H, br s), 1.0–2.5 (46H, s), 3.6 (9H, s), 3.80 (6H, t), 3.90 (6H, m), 3.95 (6H, m), 4.00 (6H, m), 4.2–4.4 (13H, m), 7.0–9.4 (12H, m) m/e Found 1388. $^{13}CC_{80}H_{106}N_8O_{13}$ (M+H)$^+$ requires 1388.

Synthesis of tetra-(1,4,7-trioxa-10-hydroxydecyl) phthalocyanine (10).

A solution of Pc 5 (300 mg, 0.01 mmol) and p-toluene sulphonic acid (20 mg) in ethanol/dichloromethane (5 ml) and 10M HCl (0.2 ml), was heated at reflux for 24 h. The solvent was removed and the resultant blue solid was eluted through a silica column by pyridine to give tetra-(1,4,7-trioxa-10-hydroxydecyl)phthalocyanine (10) (10 mg, 65%).: Found: C, 60.9; H, 6.1; N, 9.7; $C_{56}H_{66}N_8O_{16}$ requires: C,60.75; H, 6.01; N, 10.12. UV/V is (DMSO, $\lambda_{max}$ nm) 702, 666, 641, 606, 394, 340. $\delta_H$ (500 MHz, solvent DMSO) −3.5 (2H, br s), 3.82 (8H, s), 3.93 (8H, t), 4.16 (8H, m), 4.49 (6H, m), 4.5–4.6 (8H, br m), 7.0–8.5 (12H, m) m/e Found 1107. $^{13}CC_{80}H_{106}N_8O_{13}$ (M+H)$^+$ requires 1107.

SERIES 2

Synthesis of 2,3,9,10,16,17-hexa(dodecyloxy)-23-(1,4,7,10,13,16,19,22,25-nonaoxahexacosyl)-phthalocyanine (12).

To a stirred solution of 4-(1,4,7,10,13,16,19,22,25-nonaoxahexacosyl)phthalonitrile (150 mg, 0.29 mmol) and 4,5-bis(dodecyloxy)phthalonitrile (1.5 g, 3.0 mmol) in refluxing pentanol was added an excess of lithium metal (0.2 g). The reaction mixture was stirred at reflux for a further 3 h, cooled and a solution of acetic acid (10 ml) in acetone (50 ml) added. The resultant green precipitate was collected by filtration and washed with acetone (3×50 ml). The crude product mixture was applied to a column of silica gel and the symmetrical octa-(dodecyloxy)phthalocyanine eluted with warm toluene. Further elution of the silica with a solvent mixture of toluene/THF (1:1) gave a green fraction which, on removal of solvent under reduced pressure and recrys-tallisation from toluene/hexane, afforded 2,3,9,10,16,17-hexa(dodecyloxy)-23-(1,4,7,10,13,16,19,22,25-nonaoxahexacosyl)-phthalocyanine (12)(200 mg, 35%).
Found: C, 72.4; H, 9.8; N, 5.65; $C_{121}H_{196}N_8O_{15}$ requires: C.72.56; H, 9.9; N, 5.6. UV/V is (toluene, nm) 702, 664, 641, 604, 420, 340. $\delta_H$ (500 MHz, solvent $C_6H_6$) −3.0 (2H, br s), 1.10 (18H, t), 1.4–1.6 (96H), 1.89 (12H, m), 2.23 (12H, m), 3.23 (3H, s), 3.42 (2H, t), 3.53 (8H, br s), 3.59 (4H, br s), 3.63 (4H, m), 3.73 (2H, t), 3.78 (2H, t), 3.86 (2H, t), 3.93 (2H, t), 4.10 (2H, t), 4.29 (12, m), 4.44 (2H, t), 4.51 (2H, t), 7.79 (1H, d), 8.6–8.9 (7H, m), 9.32 (1H, d), m/e Found 2003. $^{13}C_2C_{119}H_{196}N_8O_{15}$(M+H)$^+$ requires 2003.

The following members of Series 2 were made by similar methods—analytical data is given for each example. (11): Found: C, 74.5; H, 10.3; N, 6.4; $C_{111}H_{176}N_8O_{10}$ requires: C.74.78; H. 10.0; N, 6.3. UV/V is (toluene, nm) 702, 664, 641, 604, 420, 340. $\delta_H$ (500 MHz, solvent $C_6H_6$) −3.0 (2H, br s), 1.10 (18H, t), 1.4–1.6 (96H), 1.89 (12H, m), 2.23 (12H, m), 3.31 (3H, s), 3.61 (2H, t), 3.86 (2H, t), 3.93 (2H, t), 4.10 (2H, t), 4.29 (12, m), 4.44 (2H, t), 4.51 (2H, t), 7.79 (1H, d), 8.6–18.9 (7H, m), 9.32 (1H, d), m/e Found 1783. $^{13}C_2C_{109}H_{176}N_8O_{10}$ (M+H)$^+$ requires 1783.

(13): Found: C, 70.92; H,10.20 N, 5.08; $C_{129}H_{212}N_8O_{19}$ requires: C.71.10; H, 9.81; N, 5.14. UV/V is (toluene, nm) 702, 664, 641, 604, 420, 340. $\delta_H$ (500 MHz, solvent $C_6H_6$) −3.0 (2H, br s), 1.10 (18H, t), 1.4–1.6 (96H), 1.89 (12H, m), 2.23 (12H, m), 3.23 (3H, s), 3.42 (2H, t), 3.55 (24H, br s), 3.59 (4H, br s), 3.63 (4H, m), 3.73 (2H, t), 3.78 (2H, t), 3.86 (2H, t), 3.93 (2H, t) 4.10 (2H, t), 4.29 (12, m), 4.44 (2H, t), 4.51 (2H, t), 7.79 (1H, d), 8.6–8.9 (7H, m), 9.32 (1H, d).

(14): Found: C, 77.15; H, 9.6; N, 5.6; $C_{129}H_{188}N_8O_{10}$ requires: C.77.05; H, 9.42; N, 5.57. UV/V is (toluene, $\lambda_{max}$ nm) 702, 664, 641, 604, 420, 340. $\delta_H$ (500 MHz, solvent $C_6H_6$) −3.0 (2H, br s), 1.10 (18H, t), 1.4–1.6 (96H), 1.89 (12H, m), 2.23 (12H, m), 3.51 (2H, t), 3.86 (2H, t), 3.93 (2H, t), 4.10 (2H, t), 4.29 (12, m), 4.44 (2H, t), 4.51 (2H, t), 7–7.5 (9H, m), 7.79, (1H, d), 7.83 (6H, d) 8.6–8.9 (7H, m), 9.32 (1H, d), m/e Found 2010. $^{13}C_2C_{127}H_{188}N_8O_{10}$ (M+H)$^+$ requires 2011.

(15): Found C, 80.1%; H, 11.3%; N, 5.7%. $C_{135}H_{224}N_8O_4$ requires C, 80.1%; H, 11.2%; N, 5.5%). UV/V is ($\lambda_{max}$ nm, THF) 701, 665, 643, 604, 343. $\delta_H$ (500 MHz, solvent $C_6D_6$, 50° C.): −1.3 (b s, 2H), 1.01 (t, 18H), 1.3–1.8 (m, 156H), 2.15 (b m, 12H), 3.2–3.4 (s and b m, 15H), 3.60 (t, 2H), 3.76 (t, 2H), 3.83 (t, 2H), 3.88 (t, 2H), 4.02 (b m, 2H), 4.37 (b m, 2H), 7.78 (d, 1H), 8.85 (b s, 1H), 9.1–9.6 (m, 7H). m/e (%): found 2024. $^{13}C_2C_{133}H_{224}N_8O_4$ (M$^+$+H$^+$) requires 2023.

(16) Found C, 81.30%; H, 10.70%; N, 4.89%. $C_{155}H_{240}N_8O_5$ requires C, 81.10%; H, 10.54%; N, 4.88%). $\delta_H$ (500 MHz, solvent $C_6D_6$, 60° C.): −2.6 (b s, 2H), 1.00 (m, 18H), 1.3–1.7 (m, 144H), 1.78 (b m, 12H), 2.14 (b m, 12H), 3.33 (b m, 12H), 3.43 (t, 2H), 3.68 (t, 2H), 3.72 (m, 2H), 3.76 (m, 2H), 3.83 (m, 4H), 3.97 (b m, 2H), 4.35 (b m, 2H), 7.70 (d, 6H), 7.79 (d, 1H), 9.12 (b s, 1H), 9.4–9.7 (m, 7H). m/e found 2054. $^{13}C_2C_{134}H_{225}N_8O_5$ (M$^+$-(Ph$_3$C)+H$^+$) requires 2052

Synthesis of 2,3,9,10,16,17-hexahexadecyl-23-(1,4,7,10-tetraoxa-12-hydroxydodecyl)phthalocyanine (17).

HCl (10M, 0.2 ml) was added to a refluxing THF (10 ml) solution of Pc 16 (200 mg, 0.095 mmol). The mixture was heated for 1 hour, the solvent removed and the resulting blue solid eluted through a silica column (eluent: toluene/methanol, 19:1, 50° C., R$_f$=0.6) and precipitated into methanol. Yield=160 mg (82%). (Found C, 78.8%; H, 10.8%; N, 5.4%. $C_{136}H_{226}N_8O_5$ requires C, 79.5%; H, 11.1%; N, 5.5%). $\delta_H$ (ppm, 500 MHz, $C_6D_6$, 60° C.): −0.8 (b s, 2H), 1.00 (t, 18H), 1.3–1.7 (m, 144H), 1.78 (b m, 12H), 2.14 (b m, 12H), 3.33 (b m, 12H), 3.51 (t, 2H), 3.61 (m, 2H), 3.66 (m, 2H), 3.73 (m, 4H), 3.82 (t, 2H), 3.98 (b t, 2H), 4.40 (b m, 2H), 7.82 (d, 1H), 9.08 (b s, 1H), 9.4–9.7 (m, 7H).

SERIES 3

Synthesis of 2,3,9,10,16,17,23,24-octa(1,4,7,10-tetraoxaundecyl)phthalocyanine (18)

To a stirred solution of 4,5-bis(1,4,7,10-tetraoxaundecyl) phthalonitrile (0.5 g, 1.1 mmole) in dry 3,6,9-trioxadecan-1-ol (1 mL) at 140° C. was added an excess of lithium metal (0.05 g). Heating was continued for 4 h, then acetic acid (0.5 mL) was added to the green reation mixture. After cooling to room temperature, the reaction mixture was placed on a column of silica and washed with ethanol (100 mL), ethanol/water (1:1) (100 mL) and finally ethanol (100 mL). The green band was then eluted from the column with ethanol/dichloromethane (1:1) (50 mL). Evaporation of the solvent gave a dark green oily solid which was dissolved in a minimum of dichloromethane and reprecipitated from hexane to give 2,3,9,10,16,17,23,24-octa(1,4,7,10-tetraoxaundecyl)phthalocyanine (18) as a dark green oily solid (0.125 g, 25%). (Found: C, 58.60%; H, 7.00%; and N, 6.15%. $C_{88}H_{130}N_8O_{32}$ requires C, 58.33%; H, 7.23%; N, 6.18%.) $\lambda_{max}$ ($CH_2Cl_2$): 698, 664, 642, 600, 422, and 348. $\delta_H$ (500 MHz, solvent $C_6D_6$, 60° C.): –3.20 (2H, br s), 3.37 (24H,s), 3.64 (16H, t), 3.82 (16 H, t), 3.93 (16H, t), 4.08 (16H, t), 4.25 (16H, t), 4.61 (16H, br t), and 8.71 (8H, br s). m/e 1813 $^{13}CC_{87}H_{130}O_{32}N_8(M^++H^+)$ requires 1812.

The following members of Series 3 were made by similar methods—analytical data is given for each example.

(19): Found: C, 55.8%; H, 8.0%; and N, 2.9%. $C_{168}H_{290}N_8O_{72}$ requires C, 56.4%; H, 8.2%; N, 3.1%.) $\lambda_{max}$ ($CH_2Cl_2$): 698, 664, 642, 600, 422, and 348. $\delta_H$ (500 MHz, solvent $C_6D_6$, 60° C.): –3.20 (2H, br s), 3.37 (24H,s), 3.5 (160H, s), 3.64 (16H, t), 3.82 (16H, t), 3.93 (16H, t), 4.08 (16H, t), 4.25 (16H, t), 4.61 (16H, br t), and 8.73 (8H, br s).

(20) Found: C, 55.6%; H, 8.2%; and N, 2.2%. $C_{232}H_{418}N_8O_{104}$ requires C, 55.91%; H, 8.45%; N, 2.25%.) $\lambda_{max}$ ($CH_2Cl_2$): 698, 664, 642, 600, 422, and 348. $\delta_H$ (500 MHz, solvent $C_6D_6$, 60° C.): –3.20 (2H, br s), 3.37 (24H,s), 3.5 (288H, s), 3.64 (16H, t), 3.82 (16H, t), 3.93 (16H, t), 4.08 (16H, t), 4.25 (16H, t), 4.61 (16H, br t), and 8.73 (8H, br s).

(21) Found: C, 54.36%; H, 8.41%; and N, 1.9%. $C_{296}H_{546}N_8O_{136}$ requires C, 55.6%;H, 8.6%; N, 1.8%.) $\lambda_{max}$ ($CH_2Cl_2$): 698, 664, 642, 600, 422, and 348. $\delta_H$ (500 MHz, solvent $C_6D_6$, 60° C.): –3.20 (2H, br s), 3.37 (24H,s), 3.5 (416H, s), 3.64 (16H, t), 3.82 (16H, t), 3.93 (16H, t), 4.08 (16H, t), 4.25 (16H, t), 4.61 (16H, br t), and 8.73 (8H, br s).

Synthesis of Phthalocyanines 22, 23, 24 and 25

Dry ammonia gas was bubbled through a stirred solution of 4,5-bis(1,4,7,10-tetraoxaundecyl)phthalonitrile (0.5 g, 1.1 mmol), 4,5-bis(dodecyloxy)phthalonitrile (0.55 g, 1.1 mmol) and sodium methoxide (5 mg) in dry 2-dimethylaminoethanol (5 ml), at 60° C., for 2 h. The temperature of the reaction was then raised to 130° C. for 24 h. On cooling, the green product mixture was placed on a column of silica and washed with ethanol (100 ml) and ethanol/$H_2O$ (1:1, 100 ml) then ethanol (100 ml) and the green fraction was removed from the column with dichloromethane and ethanol (1:1). The resultant green mixture was then applied to a fresh column of silica and eluted with an increasing amount of THF relative to toluene. The first fraction (15 mg, 1.4% yield) was collected and found to be identical ($R_f$=0.8, toluene) to a previously prepared sample of 2,3,9,10,16,17,23,24-octadodecyloxy phthalocyanine.

The second fraction was collected and applied to a fresh silica column (eluent: toluene/THF, 4:1) and was reprecipitated from toluene into MeOH to give 2,3,9,10,16,17-hexa(dodecyloxy)-23,34-di(1,4,7,10-tetraoxyundecyl) phthalocyanine (22) as a green semi-solid (3.2 mg, 0.3%). Transition temperatures: 80° C. (K-$D_{ho}$), 315° C. ($D_{ho}$-I). (Found C, 72.90; H, 9.73; N, 5.81. $C_{118}H_{190}N_8O_{14}$ requires C, 72.87; H, 9.85; N, 5.76). $\lambda_{max}$($CH_2Cl_2$) 700, 664, 602, 426, 348. $\delta_H$ (500 MHz, solvent $C_{D6}$, 60° C.): –2.50 (2H,br s), 1.05 (18H, t), 1.42–1.72 (96H, m), 1.86 (12H, pent), 2.23 (12H, m), 3.32 (6H, s), 3.60 (4H, t), 3.79 (4H, t), 3.89 (4H, t), 4.02 (4H, t), 4.16 (4H, t), 4.40 (12H, m), 4.53 (4H, br t), 8.87 (2H, br s), 8.92 (2H, br), 8.93 (2H, br s), and 8.97 (2H, br s). m/e found 1945, $^{13}CC_{117}H_{190}N_8O_{14}(M^++H^+)$ requires 1945. The third fraction was collected and applied to a fresh silica column (eluent: toluene/THF, 1:1, $R_f$=0.4) and was reprecipitated from $CH_2Cl_2$ into ethanol to give 2,3,16,17-tetra(dodecyloxy)-7,10,23,24-tetra(1,4,7,10 tetraoxaundecyl)phthalocyanine(23) as a green oily solid (7.1 mg, 0.7%) Transition temperatures: 43° C. (K-$D_{ho}$), 305° C. ($D_{ho}$-I) (Found: C, 68.10%; H, 8.90%; and N, 6.00%. $C_{108}H_{170}O_{20}N_8$ requires: C, 68.25%; H, 9.02%; N, 5.90%). $\lambda_{max}$ ($CH_2Cl_2$): 700, 664, 640, 604, 427, and 345. $\delta_H$ (500 MHz, solvent $C_6D_6$, 60° C.): –2.5 (2H, br s), 1.05 (12H, t), 1.38–1.72 (64H, br m), 1.86 (8H, pent), 2.23 (8H, pent), 3.32 (12H, s), 3.60 (8H, t), 3.79 (8H, t), 3.89 (8H, t), 4.01 (8H, t), 4.15 (8H, br t), 4.44 (8H, br t), 4.54 (8H, br t), 8.93 (4H, br s) and 8.95 (4H, br s). m/e found 1900. $^{13}CC_{107}H_{170}O_{20}N_8(M^++H^+)$ requires 1900. The fourth fraction was collected and applied to a fresh silica column (eluent: toluene/THF, 1:4, $R_f$=0.6) and was reprecipitated from $CH_2Cl_2$ into ethanol to give 2,3,9,10-tetra(dodecyl)-16,17,23,24-tetra(1,4,7,10-tetraoxaundecyl) phthalocayanine (24) as a green semi-solid (13.3 mg, 1.3%). Transition temperatures: 39° C. (K-$D_{ho}$), 306° C. ($D_{ho}$-I). (Found: C, 68.1%; H, 9.00%; and N, 6.10%. $C_{108}H_{170}O_{20}N_8$ requires: C, 68.25%; H, 9.02%; N, 5.90%. $\lambda_{max}$/nm ($CH_2Cl_2$): 698, 664, 640, 602, 425, and 350. $\delta_H$ (500 MHz, solvent $C_6D_6$, 60° C.): –2.45 (2H, br s), 1.04 (12H, t), 1.40–1.72 (64H, br m), 1.86 (8H, pent), 2.22 (8H, sept), 3.32 (12H, s), 3.60 (8H, t), 3.79 (8H, t), 3.90 (8H, t), 4.02 (8H, t), 4.16 (4H, t), 4.20 (4H, t), 4.41 (4H, br t), 4.45 (4H, br t), 4.53 (4H, br t), 4.60 (4H, br t), 8.90 (4H, br s), 8.96 (2H, br s), and 8.98 (2H, br s). m/e found 1900. $^{13}CC_{107}H_{170}O_{20}N_8$ ($M^++H^+$) requires 1900. The fourth fraction was collected and applied to a fresh silica column (eluent: toluene/THF, 1:9, $R_f$=0.6) and was reprecipitated from $CH_2Cl_2$ into ethanol to give 2,3-di(dodecyloxy)-9,10,16,17,23,24-hexa(1,4,7,10-tetraoxyundecyl)phthalocyanine (25) as a green oily solid (11.6 mg, 1.1%), Transition temperatures: 23° C. (K-$D_{ho}$), 295° C. ($D_{ho}$-I), (Found: C, 63.10%; H, 8.15%; and N, 6.00%. $C_{98}H_{150}O_{26}N_8$ requires: C, 63.40%; H, 8.15%; N, 6.05%.), $\alpha_{max}$/nm ($CH_2Cl_2$): 698, 664, 640, 602, 425 and 350. $\delta_H$ (500 MHz, solvent $C_6D_6$, 60° C.): –3.00 (2H, br s), 1.05 (6H, t), 1.42–1.74 (32H, br m), 1.89 (4H, pent), 2.26 (4H, pent), 3.34 (18H, s), 3.62 (12H, t), 3.81 (12H, t), 3.93 (12H, t), 4.06 (12H, t), 4.20 (4H, t), 4.24 (8H, t), 4.45 (4H, br t), 4.55 (4H, br t), 4.61 (8H, br t), 8.79 (2H, br s), 8.81 (2H, br s), 8.84 (2H, br s), and 8.87 (2H, s), m/e found 1856. $^{13}CC_{97}H_{150}O_{26}N_8$ ($M^++H^+$) requires 1856. A sixth fraction ($R_f$=0.1, eluent THF) proved to be 2,3,9,10,16,17,23,24-octa (1,4,7,10-trioxaundecyl)phthalocyanine (18) (4.1 mg, 0.4%) identical to a previously prepared sample.

Synthesis of phthalocyanines 26, 27, 28 and 29

To a rapidly stirred mixture of 4,5-bis(1,4,7,10-tetraoxaundecyl)phthalonitrile (0.452 g, 1.00 mmol) and 4,5-bis(hexadecyl)phthalonitrile (0.577 g, 1.00 mmol) in triethyleneglycol monomethyl ether (5 ml), at 140° C. under nitrogen, was added excess lithium metal (0.1 g). Heating and stirring were continued for 4 h. On cooling, acetic acid (10 ml) and acetone (100 ml) were added to the reaction mixture and the resultant precipitate collected. The green product mixture was placed on a column of silica and washed with ethanol (100 ml) and ethanol/H$_2$O (1:1, 100 ml) then ethanol (100 ml) and the green fraction was removed from the column with dichloromethane and ethanol (1:1), at 50° C. The product mixture was dissolved in a minimum of warm toluene (5 ml) and applied to a column of silica gel and eluted, at 50° C., with an increasing amount of THF relative to toluene. The first fraction (15 mg, 1.5% yield) was collected and found to be identical ($R_f$=0.8, toluene) to a previously prepared sample of 2,3,9,10,16,17,23,24-octa (hexadecyl)phthalocyanine. The second fraction was collected and applied to a fresh silica column (eluent: toluene/THF, 4:1, 50° C., $R_f$=0.5) and recrystallised from hexane:dichloromethane (9:1) to afford 2,3,9,10,16,17-hexa (hexadecyl)-23,24-di(1,4,7,10-tetraoxaundecyl) phthalocyanine (26) (100 mg, 10%). Transition temperatures: 85° C. (K-D$_{rd}$), 94° C. (D$_{rd}$-D$_{hd}$), 208° C. (D$_{hd}$-I). (Found C, 77.50; H, 10.80; N, 5.05. C$_{160}$H$_{274}$N$_8$O$_8$ requires C, 78.0; H, 11.0; N 5.1). $\lambda_{max}$(toluene) 704, 668, 648, 608, 422, 348. $\delta_H$ (500 MHz, solvent C$_6$D$_6$, 60° C.): −0.5 (2H, broad s), 1.00 (18H t), 1.3–1.8 (144H, m), 1.78 (12H, m), 2.13(12H, broad s), 3.31 (18H, m), 3.58 (4H, t), 3.75 (4H, m), 3.82 (4H, t), 3.92 (4H, t), 4.04 (4H, t), 4.45 (4H, broad s), 9.12 (2H, broad s), 9.4–9.8 (6H, broad m). m/e found 2185. $^{13}$C$_2$C$_{158}$H$_{274}$N$_8$O$_8$(M$^+$+H$^+$) requires 2185. The third fraction was collected and applied to a fresh silica column (eluent: heptane/THF, 1:1, 50° C., $R_f$=0.4) and recrystallised from hexane:dichloromethane (9:1) to afford 2,3,16,17-tetra (hexadecyl)-9,10,23,24-tetra(1,4,7,10-tetraoxaundecyl) phthalocyanine (27) (24 mg, 2.4%), Transition temperatures: 78° C. (K-D$_{rd}$), 240° C. (D$_{rd}$-I). (Found C, 72.30; H, 9.90; N, 5.40. C$_{124}$H$_{202}$N$_8$O$_{16}$ requires C, 72.3; H, 9.9; N 5.4). $\lambda_{max}$(toluene) 704, 668, 648, 608, 422, 348. $\delta_H$ (500 MHz, solvent C$_6$D$_6$, 60° C.): −1.4 (2H, broad s), 1.00 (12H t), 1.3–1.8 (96H, m), 1.78 (8H, m), 2.12 (8H, broad s), 3.26 (8H, broad s), 3.31 (12H, s), 3.61 (8H, t), 3.79 (8H, t), 3.87 (8H, t), 3.99 (8H, t), 4.13 (8H, broad t), 4.50 (8H, broad s), 9.05 (4H, broad s), 9.29 (4H, broad s). m/e found 2060. $^{13}$CC$_{123}$H$_{202}$N$_8$O$_{16}$(M$^+$+H$^+$) requires 2060. The fourth fraction was collected and applied to a fresh silica column (eluent: hexane/THF, 1:4, 20° C., $R_f$=0.6) and recrystallised from hexane:dichloromethane (9:1) to afford 2,3,9,10-tetra (hexadecyl)-16,17,23,24-tetra(1,4,7,10-tetraoxaundecyl) phthalocyanine (28) (52 mg, 5.2%), Transition temperatures: 78° C. (K-D$_{rd}$), 178° C. (D$_{rd}$-D$_{hd}$), 211° C. (D$_{hd}$-I). (Found C, 72.40; H, 9.90; N, 5.35. C$_{124}$H$_{202}$N$_8$O$_{16}$ requires C, 72.3; H, 9.9; N 5.4). $\lambda_{max}$(toluene) 704, 668, 648, 608, 422, 348. $\delta_H$ (500 MHz, solvent C$_6$D$_6$, 60° C.): −1.3 (2H, broad s), 1.00 (12H t), 1.3–1.8 (96H, m), 1.82 (8H, m), 2.16 (8H, broad s), 3.3–3.4 (20H, m), 3.59 (8H, m), 3.76 (8H, m), 3.86 (8H, m), 3.97 (8H, m), 4.11 (8H, broad t), 4.45–4.55 (8H, broad m), 8.95 (4H, broad m), 9.4–9.6 (4H, broad t). m/e found 2060. $^{13}$CC$_{123}$H$_{202}$N$_8$O$_{16}$(M$^+$+H$^+$) requires 2060. The fifth fraction was collected and applied to a fresh silica column (eluent: toluene/THF, 1:4, 20° C., $R_f$=0.2) and recrystallised from hexane to afford 2,3-di(hexadecyl)-9,10, 16,17,23,24-hexa(1,4,7,10-tetraoxaundecyl)phthalocyanine (28) (25 mg, 2.5%), Transition temperatures: 43° C. (K-D$_{rd}$), 175° C. (D$_{rd}$-D$_{hd}$), 229° C. (D$_{hd}$-I). (Found C, 65.70; H, 8.60; N, 5.60. C$_{106}$H$_{166}$N$_8$O$_{24}$ requires C, 65.8; H, 8.6; N, 5.8). $\lambda_{max}$(toluene) 704, 668, 648, 608, 422, 348. $\delta_H$ (500 MHz, solvent C$_6$D$_6$, 60° C.): −1.9 (2H, broad s), 1.00 (6H, t), 1.2–1.75 (48H, m), 1.83 (4H, m), 2.18 (4H, broad s), 3.3–3.4 (22H, broad m), 3.61 (12H, m), 3.79 (12H, m), 3.89 (12H, m), 4.01(12H, m), 4.16 (12H, broad t), 4.5–4.6 (12H, broad m), 8.6–9.1 (6H, broad m), 9.41 (2H, broad m). m/e found 1936. $^{13}$CC$_{105}$H$_{166}$N$_8$O$_{24}$(M$^+$+H$^+$) requires 1936. A sixth fraction (R$_f$=0.1, eluent THF) proved to be a trace amount of 2,3,9,10,16,17,23,24-octa(1,4,7,10-trioxaundecyl)phthalocyanine (18).

Preparation of copper derivative of Pc 20–(Pc 30)

A solution of Pc 20 (50 mg) and copper (II) acetate (10 mg) in pentanol (5 ml) was refluxed for 2 h. On cooling, the reaction mixture was eluted through a silica column using ethanol/dichloromethane as eluent. The solvent was removed under reduced pressure to afford Pc (30) (43 mg, 85%). (Found C, 55.5; H, 7.9; N, 3.1. C$_{168}$H$_{290}$N$_8$O$_{24}$.Cu requires C, 55.46; H, 8.18; N, 3.08). $\lambda_{max}$(toluene) 678, 640, 610, 582, 414, 346.

SERIES 4

Preparation of 4-dodecyloxy-5-(1,4,7,10-tetraoxaundecyl)-phthalonitrile a. 2-dodecyloxyphenol A mixture of catechol (11 g, 100 mmole), bromododecane (32.4 g, 130 mmoles) and potassium carbonate (18.2 g, 130 mmole) in dry DMF (100 ml) was stirred and heated at 60° C. for 48 h. The mixture was poured into water (500 ml) and extracted with diethyl ether (3×100 ml). The combined ether extracts were washed with saturated sodium chloride solution (2×100 ml) and dried with anhydrous magnesium sulphate. The ether was removed to give a solid. Distillation at reduced pressure gave 2-dodecyloxyphenol (11.4 g, 41%), b.p. 175° C./0.5 mmHg. (Found C, 77.80; H, 10.80; C$_{18}$H$_{30}$O$_2$ requires C,77.65; H, 10.86; MS (CI) m/e 296 (M$^+$+NH$_4^+$). $\delta_H$ (200 MHz, CDCl$_3$) 0.90(t, 3H), 1.28(br s, 18H), 1.82(q, 2H), 4.04(t, 2H), 5.70(s, 1H) and 6.85(m, 4H) and Catechol bis-decyl ether (11.2 g, 25%), b.p. 225° C./0.5 mmHg, m.p. 46° C. (Lit. 46° C.)$^5$.

b. 1-dodecyloxy-2-(1,4,7,10-tetraoxaundecyl)benzene

A mixture of 2-dodecyloxyphenol (4.75 g, 17.1 mmole), 3,6,9-trioxadecyl-p-toluene sulphonate$^{24}$ (6 g, 18.9 mmole), dry acetone (50 ml) and anhydrous potassium carbonate (2.6 g, 18.9 mmole) was stirred and heated to reflux under a nitrogen atmosphere for 48 h. Upon cooling the reaction mixture was filtered and the acetone removed under reduced pressure. Distillation of the resultant oil, under reduced pressure, gave 1-dodecyloxy-2-(1,4,7,10-tetraoxaundecyl) benzene as a clear oil (5.4 g, 74%), b.p. 245° C./0.4 mmHg; MS (CI) m/e 442 (M$^+$+NH$_4^+$). $\delta_H$ (200 MHz, CDCl$_3$) 0.88(t, 3H), 1.26(br s, 18H), 1.80(q, 2H), 3.38 (s, 3H), 3.50–3.80 (m, 8H), 3.87 (t, 2H), 3.98 (t, 2H), 4.17(t, 2H) and 6.90(s, 4H) which was used in the next step without further purification.

c. 1,2-dibromo-4-dodecyloxy-5-(1,4,7,10-tetraoxaundecyl) benzene

To a stirred solution of 1-dodecyloxy-2-(1,4,7,10-tetraoxaundecyl)benzene (5 g, 11.8 mmole) in dichloromethane (50 ml), cooled to 0° C., was added a solution of bromine (3.95 g, 24.3 mmole) in dichloromethane (10 ml), dropwise. The reaction was allowed to warm to room temperature and then the solution was washed with saturated sodium sulphite solution (2×20 ml) and dried over anhydrous magnesium sulphate. The solvent was removed under reduced pressure to give 1,2-dibromo-4-dodecyloxy-5-(1,4, 7,10-tetraoxaundecyl)benzene as a clear oil (6.5 g, 95%) (Found C, 51.33; H, 7.47. C$_{25}$H$_{42}$Br$_2$O$_5$ requires C, 51.55; H, 7.27); MS (CI) m/e 580 (M$^+$+NH$_4^+$), 582 (M$^+$+2+NH$_4^+$), 584 (M$^+$+4+NH$_4^+$); $\delta_H$ (200 MHz, CDCl$_3$) 0.88(t, 3H), 1.26(br s, 18H), 1.79(q, 2H), 3.38 (s, 3H), 3.66 (m, 8H), 3.85 (t, 2H), 3.93 (t, 2H), 4.13(t, 2H), 7.06 (s, 1H), and 7.13 (s, 1H) which was used in the next step without further purification.

d. 4-dodecyloxy-5-(1,4,7,10-tetraoxaundecyl)-phthalonitrile

A mixture of 1,2-dibromo-4-dodecyloxy-5-(1,4,7,10-tetraoxaundecyl)benzene (4.5 g, 7.7 mmole) and copper (I) cyanide (2.1 g, 23 mmoles) in anhydrous DMF (50 ml) was heated and stirred at 150° C. for 48 h under a nitrogen atmosphere. The mixture was carefully poured into rapidly stirred concentrated aqueous ammonia solution (300 ml). After 1 h, the precipitate was filtered and washed with ammonia solution (50 ml) and water (200 ml). The resultant solid was dried and then passed down a silica column (ethyl acetate/petrol, 2:5) to give 4-dodecyloxy-5-(1,4,7,10-tetraoxaundecyl)-phthalonitrile as white needles (1.7 g, 47%), m.p. 38°–40° C.(recrystallised from methanol/water). (Found C, 68.20; H, 9.00; N, 6.10. $C_{27}H_{42}N_2O_5$ requires C,68.32; H, 8.92; N, 5.90); MS (CI) m/e 492 ($M^+ + NH_4^+$); $\delta_H$ (200 MHz, $CDCl_3$) 0.85(t, 3H), 1.23(br s, 18H), 1.83(q, 2H), 3.35 (s, 3H), 3.63 (m, 8H), 3.89 (t, 2H), 4.03 (t, 2H), 4.23(t, 2H), 7.12 (s, 1H), and 7.23 (s, 1H) and 4-dodecyloxy-5-(1,4,7,10-tetraoxaundecyl)phthalimide (0.27 g, 6%) as small white needles, m.p. 73°–74° C. (recrystallised from methanol/water). (Found C, 65.70; H, 8.78; N, 2.70, $C_{27}H_{43}NO_7$ requires C.65.69; H, 8.78; N, 2.70); MS (CI) m/e 511 ($M^+ + NH_4^+$); $\delta_H$ (200 MHz, $CDCl_3$) 0.85(t, 3H), 1.27(br s, 18H), 1.85(q, 2H), 3.38 (s, 3H), 3.66 (m, 8H), 3.93 (t, 2H), 4.09 (t, 2H), 4.27(t, 2H), 7.27 (s, 1H), 7.30 (s, 1H) and 7.34 (s, 1H).

Preparation of tetra-(dodecyloxy)-tetra(tetraoxaundecyl) phthalocyanine (31)

Dry ammonia gas was bubbled through a stirred solution of 4-dodecyloxy-5-(1,4,7,10-tetraoxaundecyl)phthalonitrile (300 mg, 0.63 mmoles) and sodium methoxide (5 mg) in dry 2-dimethylaminoethanol (5 ml), at 60° C., for 2 h. The temperature of the reaction was then raised to 130° C. for 24 h. On cooling, the product mixture was placed on a column of silica and washed with ethanol (100 ml), ethanol/$H_2O$ (1:1, 100 ml) and finally ethanol (100 ml) and the green products were eluted with dichloromethane/ethanol (1:1), collected and applied to a fresh silica column. The green fraction (eluent: toluene/THF, 4:1) was reprecipitated from $CH_2Cl_2$ into ethanol to give Pc (No) as an oily solid (59 mg, 20%).Transition temperatures: 12° C. ($K-D_{ho}$), 307° C. ($D_{ho}$-I). (Found: C, 68.1%; H, 8.7%; and N, 5.8%. $C_{108}H_{170}O_{20}N_8$ requires: C, 68.25%; H, 9.02%; N, 5.90%). $\lambda_{max}$ ($CH_2Cl_2$): 700, 664,642, 602, 425, and 345. $\delta_H$ (500 MHz, solvent $C_6D_6$, 60° C.): −2.67 (2H, br s), 1.05 (12H, t), 1.40–1.70 (64H, br m), 1.84 (8H, pentet), 2.24 (8H, m), 3.33 (12H, s), 3.61 (8H, t), 3.80 (8H, t), 3.90 (8H, t), 4.05 (8H, t), 4.18 (4H, t), 4.22 (4H, t), 4.38 (4H, br t), 4.45 (4H, br t), 4.53 (4H, br t), 4.63 (4H, br t), and 8.88 (8H, br s). m/e found 1900, $^{13}CC_{107}H_{170}O_{20}N_8(M^+ + H+)$ requires 1900.

The following phthalocyanine was made using similar methodology. (32): (Found: C, 61.95%; H, 8.5%; and N, 3.06%. $C_{194}H_{282}O_{48}N_8$ requires: C, 62.85%; H, 9.0%; N, 3.5%). $\delta_{max}$ ($CH_2Cl_2$): 700, 664, 642, 602,425, and 345. $\delta_H$ (500 MHz, solvent $C_6D_6$, 60° C.): −2.67 (2H, br s), 1.05 (12H, t), 1.40–1.70 (64H, br m), 1.84 (8H, pentet), 2.24 (8H, m), 3.33 (12H, s), 3.61 (128H, t), 3.90 (8H, t), 4.05 (8H, t), 4.18 (4H, t), 4.22 (4H, t), 4.38 (4H, br t), 4.45 (4H, br t), 4.53 (4H, br t), 4.63 (4H, br t), and 8.88 (8H, br s).

SERIES 5

Synthesis of Pcs 33, 34 and 35

To a rapidly stirred mixture of 4-(1,4,7,10-tetraoxaundecyl)phthalonitrile (0.6 g, 2.07 mmol) and 4,5-bis(hexadecyl)phthalonitrile (1.2 g, 2.08 mmol) in triethyleneglycol monomethyl ether (5 ml), at 140° C. under nitrogen, was added excess lithium metal (0.1 g). Heating and stirring were continued for 4 h. On cooling, acetic acid (10 ml) and acetone (100 ml) were added to the reaction mixture and the resultant precipitate collected. The blue product mixture was placed on a column of silica and washed with ethanol (100 ml) and ethanol/$H_2O$ (1:1, 100 ml) then ethanol (100 ml) and the green fraction was removed from the column with chloroform and ethanol (1:1), at 50° C. The product mixture was dissolved in a minimum of warm toluene (5 ml) and applied to a column of silica gel and eluted, at 50° C., with an increasing amount of THF relative to toluene. The first fraction was collected and found to be identical (Rf=0.8, toluene) to a previously prepared sample of 2,3,9,10,16,17,23,24-octa(hexadecyl) phthalocyanine. The second fraction was collected and applied to a fresh silica column (eluent: toluene/THF, 9:1, 50° C., Rf=0.7) and recrystallised from hexane/THF (9:1) to afford 2,3,9,10,16,17-hexahexadecyl-23-(1,4,7,10-tetraoxaundecyl)phthalocyanine (15) (90 mg, 2.1%). Transition temperatures: 81° C. ($K-D_{rd}$), 86° C. ($D_{rd}-D_{hd}$), 206° C. ($D_{hd}-I$). (Found C, 80.1%; H, 11.3%; N, 5.7%. $C_{135}H_{224}N_8O_4$ requires C, 80.1%; H, 11.2%; N, 5.5%). $\lambda_{max}$ (THF) 701, 665, 643, 604, 343. $\delta_H$(500 MHz, solvent $C_6D_6$, 50° C.): −1.3 (b s, 2H), 1.01 (t, 18H), 1.3–1.8 (m, 156H), 2.15 (b m, 12H), 3.2–3.4 (s and b m, 15H), 3.60 (t, 2H), 3.76 (t, 2H), 3.83 (t, 2H), 3.88 (t, 2H), 4.02 (b m, 2H), 4.37 (b m, 2H), 7.78 (d, 1H), 8.85 (b s, 1H), 9.1–9.6 (m, 7H). m/e (%): found 2024, $^{13}CC_{134}H_{224}N_8O_4$ ($M^+ + H^+$) requires 2024. The third fraction was collected and applied to a fresh silica column (eluent: toluene/THF, 17:3, 50° C., Rf=0.3) and recrystallised from hexane/THF (9:1) to afford 2,3,16,17-tetrahexadecyl-9,23-di(1,4,7,10-tetraoxaundecyl) phthalocyanine (33) (35 mg, 1.9%). Transition temperatures: 43° C. ($K-D_{rd}$), 142° C. ($D_{rd}-D_{hd}$), 243° C. ($D_{hd}-I$). (Found C, 75.6%; H, 9.6%; N, 6.5%. $C_{110}H_{172}N_8O_8$ requires C, 76.2%; H, 10.0%; N, 6.4%). $\lambda_{max}$ (THF) 701, 667, 645, 604, 341. $\delta_H$ (500 MHz, solvent $C_6D_6$, 50° C.): −1.4 (b s, 2H), 1.00 (t, 12H), 1.3–1.8 (m, 104H), 2.0–2.3 (2 b m, 8H), 3.0–3.4 (s and 2 b m, 14H), 3.61 (t, 4H), 3.77 (t, 4H), 3.83 (t, 4H), 3.89 (t, 4H), 4.03 (b m, 4H), 4.40 (b m, 4H), 7.78 (b m, 2H), 8.9–9.5 (m, 8H). m/e (%): found 1736, $^{13}C_2C_{108}H_{172}N_8O_8$ ($M^+ + H^+$) requires 1736. The fourth fraction was collected and applied to a fresh silica column (eluent: toluene/THF, 3:2, 50° C., $R_f$=0.3) and recrystallised from hexane/THF (4:1) to afford 2,3,9,10-tetrahexadecyl16,23-di(1,4,7,10-tetraoxaundecyl)phthalocyanine (34) (94 mg, 5.2%). Transition temperatures: 81° C. ($K-D_{rd}$), 92° C. ($D_{rd}-D_{hd}$), 243° C. ($D_{hd}-I$). (Found C, 75.8%; H, 10.0%; N, 6.6%. $C_{110}H_{172}N_8O_8$ requires C, 76.2%; H, 10.0%; N, 6.4%). $\lambda_{max\ (THF)}$ 701, 667, 645, 604, 341. $\delta_H$ (500 MHz, solvent $C_6D_6$, 60° C.): −1.3 (b s, 2H), 1.00 (m, 12H), 1.3–1.9 (m, 104H), 2.14 (b m, 8H), 3.0–3.4 (m and b m, 14H), 3.59 (m, 4H), 3.75 (m, 4H), 3.81 (m, 4H), 3.86 (m, 4H), 3.96–4.08 (2 b m, 4H), 4.34–4.49 (2 b m, 4H), 7.7–7.8 (b m, 2H), 8.8–9.0 (m, 2H), 9.2–9.5 (m, 6H). m/e (%): found 1736, $^{13}C_2C_{108}H_{172}N_8O_8$ ($M^+ + H^+$) requires 1736. The fifth fraction was collected and applied to a fresh silica column (eluent: toluene/THF, 2:3, 20° C., $R_f$=0.3) and recrystallised from hexane/THF (9:1) to afford 2,3-dihexadecyl-9,16,23-tri(1,4,7,10-tetraoxaundecyl)phthalocyanine (35) (94 mg, 6.2%). Transition temperatures: 102° C. ($K-D_{hd}$), 302° C. ($D_{hd}-I$). (Found C, 69.9%; H, 9.0%; N, 7.7%. $C_{85}H_{124}N_8O_{12}$ requires C, 70.4%; H, 8.6%; N, 7.7%). $\lambda_{max}$ (THF) 701, 665, 640, 604, 391, 343. $\delta_H$ (500 MHz, solvent $C_6D_6$, 60° C.): −2.3 (b s, 2H), 1.00 (m, 6H), 1.3–1.9 (m, 52H), 2.0–2.3 (2 b m, 4H), 3.1–3.4 (m and 2 b m, 13H), 3.63 (m, 6H), 3.79 (m, 6H), 3.86 (t, 6H), 3.92 (m, 6H), 4.0–4.15 (b m, 6H), 4.25–4.55 (b m, 6H), 7.6–7.8 (b m, 3H), 8.4–8.8 (m, 3H), 9.2–9.5 (m, 6H). m/e found 1450. $C_{85}H_{124}N_8O_{12}$ (M$^+$+H$^+$) requires 1450. A sixth fraction ($R_f$=0.1, eluent THF) proved to be a trace amount of 2,9,16,23-tetra(1,4,7,10-tetraoxaundecyl)phthalocyanine (1).

Synthesis of Pcs 36, 37 and 38

To a rapidly stirred mixture of 4-(1,4,7,10,13-pentaoxa-14,14,14-triphenyltetradecyl)phthalonitrile (1.90 g, 3.45 mmol) and 4,5-bis(hexadecyl)phthalonitrile (1.99 g, 3.45 mmol) in triethyleneglycol monomethyl ether (5 ml), at 140° C. under nitrogen, was added excess lithium metal (0.1 g). Heating and stirring were continued for 4 h. On cooling, acetic acid (10 ml) and acetone (100 ml) were added to the reaction mixture and the resultant precipitate collected. The green product mixture was placed on a column of silica and washed with ethanol (100 ml) and ethanol/diethyl ether (1:1, 100 ml) then ethanol/ethyl acetate (1:1, 100 ml) and the blue fraction was removed from the column with chloroform and ethanol (1:1), at 50° C. The product mixture was dissolved in a minimum of warm toluene (5 ml) and applied to a column of silica gel and eluted, at 50° C., with an increasing amount of THF relative to toluene. The first fraction was collected and found to be identical ($R_f$=0.8, toluene) to a previously prepared sample of 2,3,9,10,16,17,23,24-octa(hexadecyl)phthalocyanine. The second fraction was collected and applied to a fresh silica column (eluent: toluene/ethyl acetate, 19:1, 50° C., $R_f$=0.6) and recrystallised from heptane to afford 2,3,9,10,16,17-hexahexadecyl-23-(1,4,7,10,13-pentaoxa-14,14,14-triphenyltetradecyl)phthalocyanine (16). Transition temperatures: 86° C. (K-D$_{hd}$), 166° C. (D$_{hd}$-I). (Found C, 81.30%; H, 10.70%; N, 4.89%. $C_{155}H_{240}N_8O_5$ requires C, 81.10%; H, 10.54%; N, 4.88%). $\delta_H$ (500 MHz, solvent $C_6D_6$, 60° C.): –0.6 (b s, 2H), 1.00 (m, 18H), 1.3–1.7 (m, 144H), 1.78 (b m, 12H), 2.14 (b m, 12H), 3.33 (b m, 12H), 3.43 (t, 2H), 3.68 (t, 2H), 3.72 (m, 2H), 3.76 (m, 2H), 3.83 (m, 4H), 3.97 (b m, 2H), 4.35 (b m, 2H), 7.70 (d, 6H), 7.79 (d, 1H), 9.12 (b s, 1H), 9.4–9.7 (m, 7H). m/e found 2055. M$^+$—(Ph$_3$C) ($^{13}C_2C_{134}H_{225}N_8O_8$)+ H$^+$ requires 2054. The third fraction was collected and applied to a fresh silica column (eluent: toluene/ethyl acetate, 9:1, 50° C., $R_f$=0.8) and recrystallised from heptane to afford 2,3,16,17-tetrahexadecyl-9,23-di(1,4,7,10,13-pentaoxa-14,14,14-triphenyltetradecyl)phthalocyanine (36) (108 mg, 2.7% yield). Transition temperatures: 41° C. (K-D$_{rd}$), 191° C. (D$_{rd}$-D$_{hd}$), 196° C. (D$_{hd}$-I). (Found C, 79.15%; H, 9.37%; N, 4.86%. $C_{150}H_{206}N_8O_{10}$ requires C, 78.97%; H, 9.10%; N 4.91%). $\lambda_{max}$ (chloroform) 706, 670, 638, 608, 380, 344. $\delta_H$ (500 MHz, solvent $C_6D_6$, 60° C.): –1.2 (b s, 2H), 1.00 (t, 12H), 1.3–1.9 (m, 104H), 2.10 and 2.20 (2 b m, 8H), 3.22 and 3.32 (2 b m, 8H), 3.44 (t, 4H), 3.70 (t, 4H), 3.74 (m, 4H), 3.78 (m, 4H), 3.87 (m, 8H), 4.01 (b m, 4H), 4.39 (b m, 4H), 7.70 (d, 12H), 7.83 (b s, 2H), 8.9–9.5 (m, 8H). m/e found 2285. $^{13}C_2C_{148}H_{206}N_8O_{10}$ (M$^+$+H$^+$) requires 2283. The fourth fraction was collected and applied to a fresh silica column (eluent: toluene/THF, 4:1, 20° C., $R_f$=0.7) and recrystallised from heptane to afford 2,3,9,10-tetrahexadecyl-16,23-di(1,4,7,10,13-pentaoxa-14,14,14-triphenyltetradecyl)phthalocyanine (37)(268 mg, 6.8%). Transition temperatures: 77° C. (K-D$_{hd}$), 152° C. (D$_{hd}$-I). (Found C, 79.06%; H, 9.12%; N, 4.80%. $C_{150}H_{206}N_8O_{10}$ requires C, 78.97%; H, 9.10%; N 4.91%). $\lambda_{max}$ (chloroform) 706, 670, 638, 608, 380, 344. $\delta_H$ (ppm, 500 MHz, $C_6D_6$, 60° C.): –1.1 (b s, 2H), 1.00 (m, 12H), 1.3–1.9 (m, 104H), 2.1–2.25 (b m, 8H), 3.2–3.4 (b m, 8H), 3.44 (m, 4H), 3.69 (m, 4H), 3.73 (m, 4H), 3.77 (m, 4H), 3.85 (m, 8H), 3.98 and 4.04 (2 b m, 4H), 4.36 and 4.46 (2 b m, 4H), 7.6–7.8 (d and b s, 14H), 8.8–9.6 (m, 8H). m/e found 2284. $^{13}C_2C_{148}H_{206}N_8O_{10}$ (M$^+$+H$^+$) requires 2283. The fifth fraction was collected and applied to a fresh silica column (eluent: toluene/THF, 4:1, 20° C., $R_f$=0.3) and recrystallised from heptane to afford 2,3-dihexadecyl-9,16,23-tri(1,4,7,10,13-pentaoxa-14,14,14-triphenyltetradecyl)phthalocyanine (38) (298 mg, 7.6%). Transition temperatures: 32° C. (K-D$_1$), 76° C. (D$_1$–D$_2$), 177° C. (D$_2$-I). (Found C, 76.44%; H, 7.38%; N, 4.86%. $C_{145}H_{172}N_8O_{15}$ requires C, 76.82%; H, 7.65%; N, 4.94%). $\lambda_{max}$ (chloroform) 706, 670, 638, 608, 380, 344. $\delta_H$ (ppm, 500 MHz, $C_6D_6$, 60° C.): –1.3 (b s, 2H), 0.99 (t, 6H), 1.3–1.9 (m, 52H), 2.0–2.3 (2 b m, 4H), 3.2–3.4 (2 b m, 4H), 3.44 (m, 6H), 3.69 (m, 6H), 3.74 (m, 6H), 3.78 (m, 6H), 3.85 (m, 12H), 3.95–4.1 (2 b m, 6H), 4.3–4.5 (2 b m, 6H), 7.6–7.9 (d and b s, 21H), 8.8–9.5 (m, 8H). m/e found 2270. $^{13}C_2C_{143}H_{172}N_8O_{15}$ (M$^+$+H$^+$) requires 2268. The sixth fraction was collected and applied to a fresh silica column (eluent: toluene/THF, 7:3, 20° C., $R_f$=0.4) and recrystallised from heptane to afford 2,9,16,23-tetra(1,4,7,10,13-pentaoxa-14,14,14-triphenyltetradecyl)phthalocyanine (6). Transition temperatures: 28° C. (G-D$_{hd}$), 222° C. (D$_{hd}$-I). (Found C, 74.33%; H, 6.12%; N, 5.01%. $C_{140}H_{138}N_8O_{20}$ requires C, 74.65%; H, 6.18%; N, 4.97%). $\delta_H$ (ppm, 500 MHz, $C_6D_6$, 60° C.): –2.5 (b s, 2H), 3.45 (m, 8H), 3.70 (m, 8H), 3.76 (m, 8H), 3.81 (m, 8H), 3.89 (m, 16H), 4.0–4.15 (2 b m, 8H), 4.3–4.5 (2 b m, 8H), 7.6–7.9 (m, 28H), 8.8–9.5 (m, 8H). m/e found 2254 $^{13}C_2C_{138}H_{138}N_8O_{20}$ (M$^+$+H$^+$) requires 2254.

Preparation of 2,3,16,17-tetrahexadecyl-9,23-di(1,4,7,10-tetraoxa-12-hydroxydodecyl)phthalocyanine (39)

2,3,16,17-tetrahexadecyl-9,23-di(1,4,7,10,13-pentaoxa-14,14,14-triphenyltetradecyl)phthalocyanine (36) (80 mg, 0.035 mmol) was refluxed in THF and to this was added 10 molar hydrochloric acid (1 ml). The mixture was heated for 1 hour, the solvent removed and the resulting blue solid was recrystallised from toluene. ($R_f$=0.2, THF/heptane, 7:3, 50° C.). Yield=39 mg (62%). Transition temperatures: 65° C. (K-D$_{rd}$), 217° C. (D$_{rd}$-D$_{hd}$), 232° C. (D$_{hd}$-I). (Found C, 74.00%; H, 9.71%; N, 6.42%. $C_{112}H_{178}N_8O_{10}$ requires C, 74.87%; H, 9.99%; N, 6.24%). $\lambda_{max}$ (chloroform) 708, 672, 642, 610, 384, 344. $\delta_H$ (ppm, 500 MHz, $C_6D_6$, 60° C.): –1.8 (b s, 2H), 1.00 (m, 12H), 1.3–1.9 (m, 104H), 2.1–2.3 (b m, 8H), 3.0–3.4 (b m, 8H), 3.5 (t, 4H), 3.67 (m, 4H), 3.71 (m, 4H), 3.78 (b m, 4H), 3.81 (t, 4H), 3.89 (m, 4H), 4.06 (b m, 4H), 4.45 (b m, 4H), 7.85 (b m, 2H), 8.8–9.5 (m, 8H). m/e found 1796. $^{13}CC_{111}H_{178}N_8O_{10}$ (M$^+$) requires 1796 The following Pcs were prepared using the same methodology 40: made from 2,3,9,10-tetrahexadecyl-16,23-di(1,4,7,10,13-pentaoxa-14,14,14-triphenyltetradecyl)phthalocyanine (37) Yield=94 mg (80%). Transition temperatures: 79° C. (K-D$_1$), 132° C. (D$_1$–D$_2$), 194° C. (D$_2$-I) (also monotropic D$_{hd}$ at 187° C. on cooling). (Found C, 74.59%; H, 9.69%; N, 6.04%. $C_{112}H_{178}N_8O_{10}$ requires C, 74.87%; H, 9.99%; N, 6.24%). $\lambda_{max}$ (chloroform) 706, 670, 638, 608, 384, 344. $\delta_H$ (ppm, 500 MHz, $C_6D_6$, 60° C.): –1.4 (b s, 2H), 1.00 (m, 12H), 1.3–1.9 (m, 104H), 2.1–2.3 (b m, 8H), 3.2–3.4 (b m, 8H), 3.55 (m, 4H), 3.65 (m, 4H), 3.69 (m, 4H), 3.77 (m, 8H), 3.86 (m, 4H), 4.02 and 4.07 (2 b m, 4H), 4.40 and 4.50 (2 b m, 4H), 7.6–7.8 (b m, 2H), 8.7–9.5 (m, 8H). m/e found 1796. $^{13}CC_{111}H_{178}N_8O_{10}$ (M$^+$) requires 1796

41: made from 2,3-dihexadecyl-9,16,23-tri(1,4,7,10,13-pentaoxa-14,14,14-triphenyltetradecyl)phthalocyanine (38). Yield=79 mg (68%). Transition temperatures: 45° C. (K-D$_1$), 80° C. (D$_1$–D$_2$), 252° C. (D$_2$–D$_3$), 272° C. (D$_3$-I), (Found C, 68.64%; H, 8.34%; N, 7.14%. $C_{88}H_{130}N_8O_{15}$ requires C, 68.63%; H, 8.51%; N, 7.28%). $\lambda_{max}$ (chloroform) 706, 670, 638, 608, 384, 346. $\delta_H$ (ppm, 500 MHz, $C_6C_6$, 60° C.): -3.3 (b s, 2H), 1.02 (m, 6H), 1.3-2.3 (m, 56H), 2.8-3.3 (2 b m, 4H), 3.65 (m, 6H), 3.74 (m, 6H), 3.78 (m, 6H,), 3.86 (m, 6H), 3.95 (m, 12H), 4.05-4.2 (2 b m, 6H, 4.25-4.6 (2 b m, 6H), 7.45-7.8 (m, 3H), 8.0-9.2 (m, 8H). Spectrum shows considerable broadening of peaks due to aggregation in benzene. m/e found 1541. $^{13}CC_{87}H_{130}N_8O_{15}$ (M⁺) requires 1541

For the above data:

$D_{ho}$=discotic hexagonal ordered $N_c$=nematic columnar $D_{hd}$=dicotic hexagonal disordered $D_{rd}$=discotic rectangular disordered In another embodiment of the invention, M in formula I may be a non-metal or non-metal compound other than silicon or compounds of silicon.

We claim:

1. A phthalocyanine of Formula I

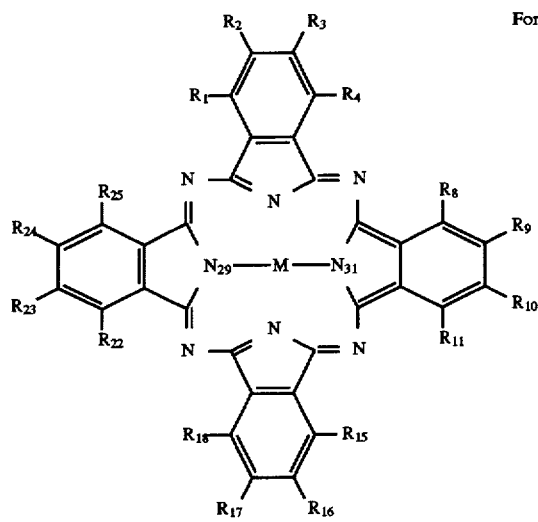

Formula I wherein

M is a metal atom, metal compound or silicon or a compound of silicon, or is 2H; one H being bonded to each of the two nitrogen atoms depicted as being bonded to M (positions 29 and 31 shown);

$R_{2,3,9,10,16,17,23,24}$ may be the same or different provided that at least one of $R_{2,3,9,10,16,17,23,24}$ has the following formula II:

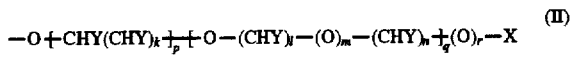

(II)

wherein Y groups are independently H, $C_{1-3}$ alkyl, halogen or CN;

k=0 or 1; l=1-10; m=0 or 1; n=1-10; p=1-10; q=1-20; r=0 or 1;

X may be one or more of the following groups:

H, Me, cholesteryl, OH, COR or COOR where R is straight or branched chain alkyl, or X may be described by the following formula:

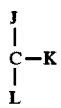

wherein C is carbon and J, K, L may be, independently of each other:

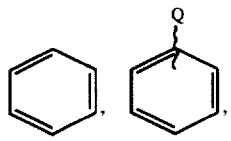

wherein Q indicates that the phenyl ring may independently carry one or more substituents including straight or branched chain alkyl or alkoxy, halogen, CN, OH, H;

$R_{1,4,8,11,15,18,22,25}$ may be independently any of the following groups:

straight or branched chain alkyl or alkoxy, H, alkene, cholesteryl, trityl,

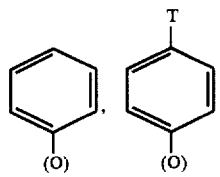

wherein (O) indicates an oxygen may or may not be present; T indicates that the phenyl or phenoxy ring may be substituted with one or more substituents selected from straight or branched chain alkyl or alkoxy, halogen, CN, OH, H:

for the cases wherein not all of $R_{2,3,9,10,16,17,23,24}$ are given by formula II then those $R_{2,3,9,10,16,17,23,24}$ groups not described by formula II may be independently any of the following groups:

straight or branched chain alkyl or alkoxy, H, alkene, cholesteryl, trityl,

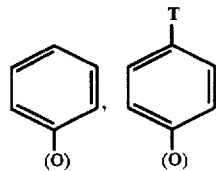

wherein (O) indicates an oxygen may or may not be present; T indicates that the phenyl or phenoxy ring may be substituted with one or more substituents selected from straight or branched chain alkyl or alkoxy, halogen, CN, OH, H.

2. A compound according to claim 1 wherein:

all Y groups=H; k=1; p=1; l=1; m=0; n=1; q=2-20; r=1;
X is chosen from one of the following groups:
Me, trityl, H;
those groups not described by formula II are independently of each other chosen from:
straight chain alkyl or alkoxy containing up to 20 carbon atoms; tert-butyl;
di-(tert-butyl)-phenoxy;

cholesteryl.

3. A compound according to claim 2 wherein M is 2H.

4. A compound according to claim 2 wherein M is a metal atom and is chosen from one of the following metals Ni, Pb, V, Pd, Co, Nb, Al, Sn, Zn, Cu, Mg, Ca, In, Ga, Fe, Eu, Lu and Ge.

5. A compound according to claim 2 wherein M is a metal compound and is an oxide or chloride or bromide of one of the following metals Ni, Pb, V, Pd, Co, Nb, Al, Sn, Zn, Cu, Mg, Ca, In, Ga, Fe, Eu, Lu and Ge.

6. A compound of the formula

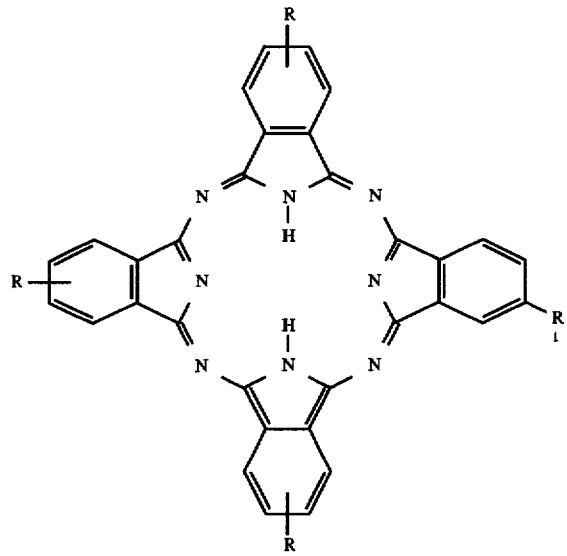

wherein R and $_1$R are independently selected from CH$_3$—(OCH$_2$CH$_2$)$_n$—O—, H—(OCH$_2$CH$_2$)$_n$—O—, Trityl—(OCH$_2$CH$_2$)$_n$—O—, Di-(tert-butyl)-phenoxy-, tert-butyl, cholesteryl, alkyl or alkoxy containing up to 20 carbon atoms; n is from 1 to 20; provided that at least one of R or $_1$R is selected from CH$_3$—(OCH$_2$CH$_2$)$_n$—O—, H—(OCH$_2$CH$_2$)$_n$—O—, Trityl—(OCH$_2$CH$_2$)$_n$—O—.

7. A compound of the formula

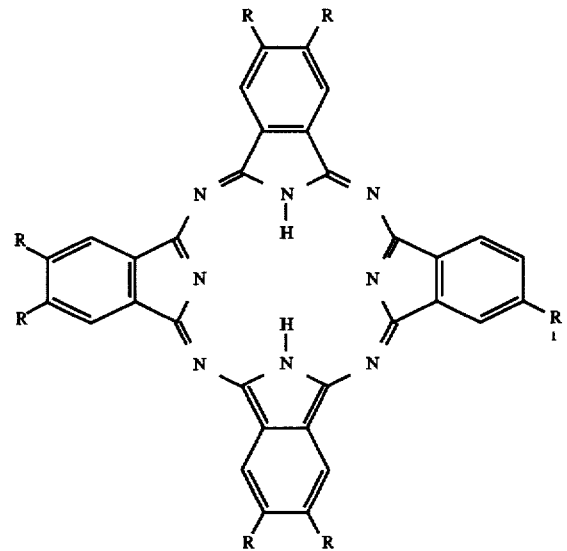

wherein R and $_1$R are independently selected from CH$_3$—(OCH$_2$CH$_2$)$_n$—O—, H—(OCH$_2$CH$_2$)$_n$—O—, Trityl—(OCH$_2$CH$_2$)$_n$—O—, Di-(tert-butyl)-phenoxy-, tert-butyl, cholesteryl, alkyl or alkoxy containing up to 20 carbon atoms; n is from 1 to 20; provided that at least one of R or $_1$R is selected from CH$_3$—(OCH$_2$CH$_2$)$_n$—O—, H—(OCH$_2$CH$_2$)$_n$—O—, Trityl—(OCH$_2$CH$_2$)$_n$—O—.

8. A compound of the formula

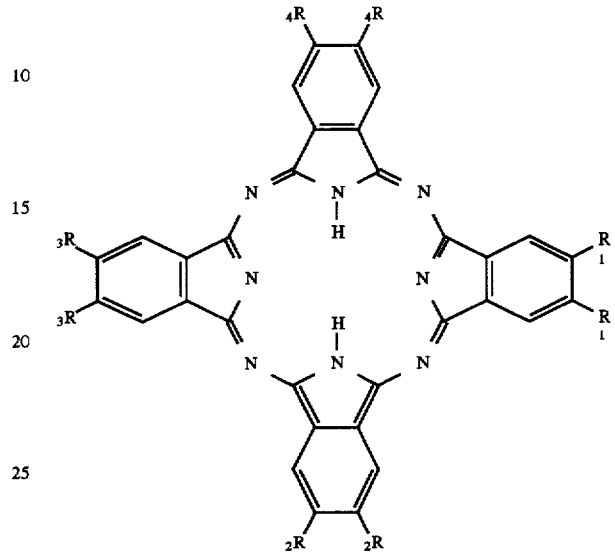

wherein $_1$R, $_2$R, $_3$R and $_4$R are independently selected from CH$_3$—(OCH$_2$CH$_2$)$_n$—O—, H—(OCH$_2$CH$_2$)$_n$—O—, Trityl—(OCH$_2$CH$_2$)$_n$—O—, Di-(tert-butyl)-phenoxy-, tert-butyl, cholesteryl, alkyl or alkoxy containing up to 20 carbon atoms; n is from 1 to 20; provided that at least one of $_1$R, $_2$R, $_3$R and $_4$R is selected from CH$_3$—(OCH$_2$CH$_2$)$_n$—O—, H—(OCH$_2$CH$_2$)$_n$—O—, Trityl—(OCH$_2$CH$_2$)$_n$—O—.

9. A compound of the formula

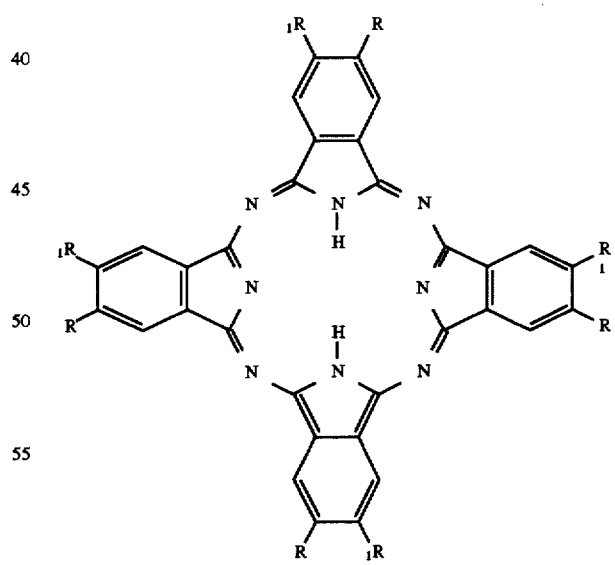

wherein R and $_1$R are independently selected from CH$_3$—(OCH$_2$CH$_2$)$_n$—O—, H—(OCH$_2$CH$_2$)$_n$—O—, Trityl—(OCH$_2$CH$_2$)$_n$—O—, Di-(tert-butyl)-phenoxy-, tert-butyl, cholesteryl, alkyl or alkoxy containing up to 20 carbon atoms; n is from 1 to 20; provided that at least one of R or $_1$R is selected from CH$_3$—(OCH$_2$CH$_2$)$_n$—O—, H—(OCH$_2$CH$_2$)$_n$—O—, Trityl—(OCH$_2$CH$_2$)$_n$—O—.

10. A compound of the formula

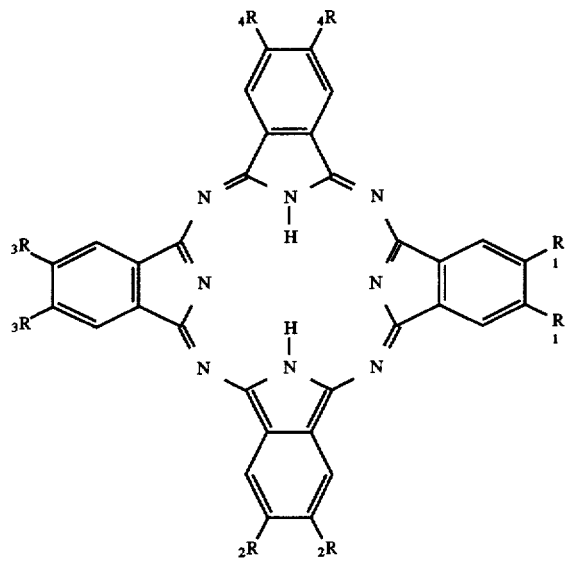

wherein $_1R$, $_2R$, $_3R$ and $_4R$ are independently selected from $CH_3$–$(OCH_2CH_2)_n$–O—, H–$(OCH_2CH_2)_n$–O—, Trityl—$(OCH_2CH_2)_n$–O—, Di-(tert-butyl)-phenoxy-, tert-butyl, cholesteryl, alkyl or alkoxy containing up to 20 carbon atoms or H; n is from 1 to 20; provided that at least one of $_1R$, $_2R$, $_3R$ and $_4R$ is selected from $CH_3$–$(OCH_2CH_2)_n$–O—, H–$(OCH_2CH_2)_n$–O—, Trityl–$(OCH_2CH_2)_n$–O—.

11. A compound of the formula

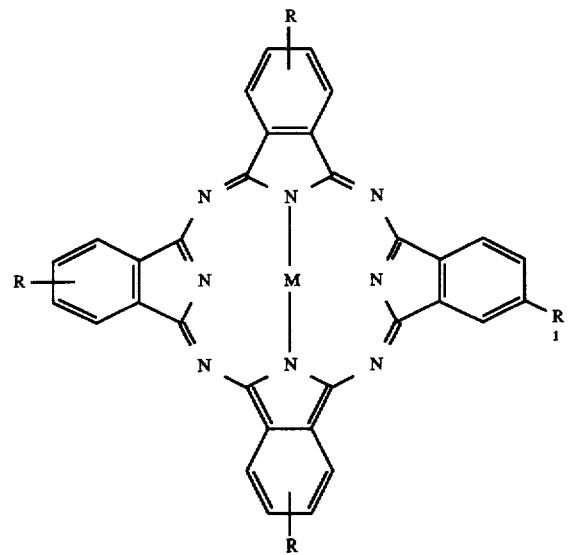

wherein M is a metal or metal compound; R and $_1R$ are independently selected from $CH_3$–$(OCH_2CH_2)_n$–O—, H–$(OCH_2CH_2)_n$–O—, Trityl–$(OCH_2CH_2)_n$–O—, Di-(tert-butyl)-phenoxy-, tert-butyl, cholesteryl, alkyl or alkoxy containing up to 20 carbon atoms; n is from 1 to 20; provided that at least one of R or $_1R$ is selected from $CH_3$–$(OCH_2CH_2)_n$–O—, H–$(OCH_2CH_2)_n$–O—, Trityl–$(OCH_2CH_2)_n$–O—.

12. A compound of the formula

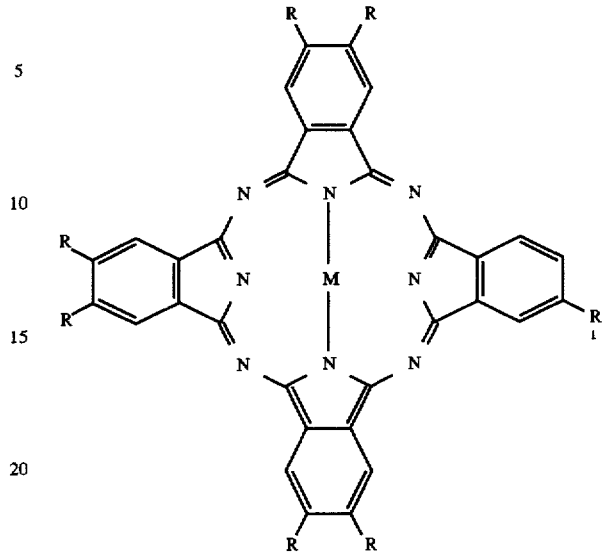

wherein M is a metal or metal compound; R and $_1R$ are independently selected from $CH_3$–$(OCH_2CH_2)_n$–O—, H–$(OCH_2CH_2)_n$–O—, Trityl-(—$OCH_2CH_2)_n$–O—, Di-(tert-butyl)-phenoxy-, tert-butyl, cholesteryl, alkyl or alkoxy containing up to 20 carbon atoms; n is from 1 to 20; provided that at least one of R or $_1R$ is selected from $CH_3$–$(OCH_2CH_2)_n$–O—, H–$(OCH_2CH_2)_n$–O—, Trityl—$(OCH_2CH_2)_n$–O—.

13. A compound of the formula

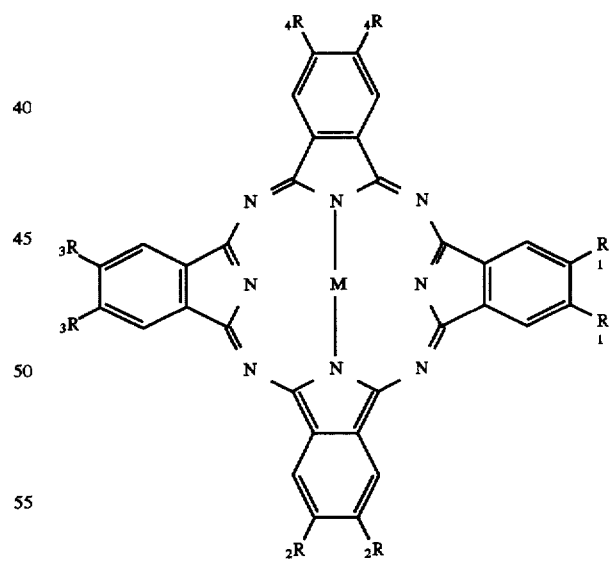

wherein M is a metal or metal compound; $_1R$, $_2R$, $_3R$ and $_4R$ are independently selected from $CH_3$–$(OCH_2CH_2)_n$–O—, H–$(OCH_2CH_2)_n$–O—, Trityl–$(OCH_2CH_2)_n$–O—, Di-(tert-butyl)-phenoxy-, tert-butyl, cholesteryl, alkyl or alkoxy containing up to 20 carbon atoms; n is from 1 to 20; provided that at least one of $_1R$, $_2R$, $_3R$ and $_4R$ is selected from $CH_3$–$(OCH_2CH_2)_n$–O—, H–$(OCH_2CH_2)_n$–O—, Trityl—$(OCH_2CH_2)_n$–O—.

14. A compound of the formula

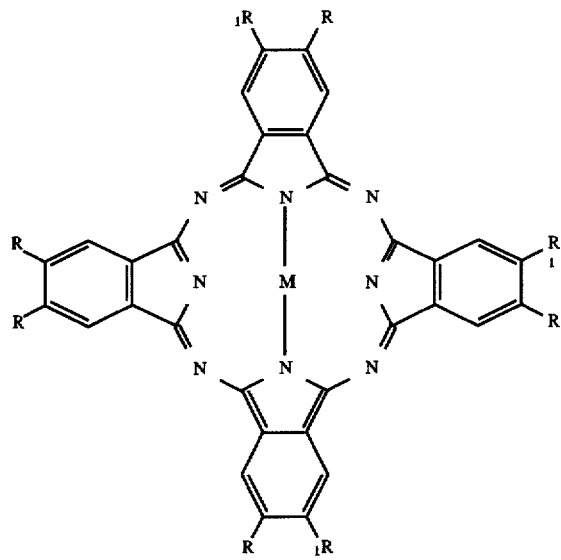

wherein M is a metal or metal compound; R and $_1$R are independently selected from $CH_3\text{-}(OCH_2CH_2)_n\text{—O—}$, $H\text{-}(OCH_2CH_2)_n\text{—O—}$, $Trityl\text{-}(OCH_2CH_2)_n\text{—O—}$, Di-(tert-butyl)-phenoxy-, tert-butyl, cholesteryl, alkyl or alkoxy containing up to 20 carbon atoms; n is from 1 to 20; provided that at least one of R or $_1$R is selected from $CH_3\text{—}(OCH_2CH_2)_n\text{—O—}$, $H\text{-}(OCH_2CH_2)_n\text{—O—}$, $Trityl\text{—}(OCH_2CH_2)_n\text{—O—}$.

15. A compound of the formula

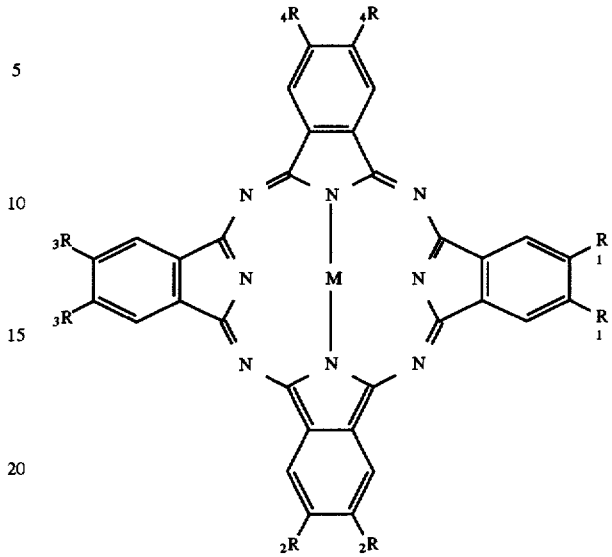

wherein M is a metal or metal compound; $_1$R, $_2$R $_3$R and $_4$R are independently selected from $CH_3\text{-}(OCH_2CH_2)_n\text{—O—}$, $H\text{-}(OCH_2CH_2)_n\text{—O—}$, $Trityl\text{-}(OCH_2CH_2)_n\text{—O—}$, Di-(tert-butyl)-phenoxy-, tert-butyl, cholesteryl, alkyl or alkoxy containing up to 20 carbon atoms or H; n is from 1 to 20; provided that at least one of $_1$R, $_2$R $_3$R and $_4$R is selected from $CH_3\text{-}(OCH_2CH_2)_n\text{—O—}$, $H\text{-}(OCH_2CH_2)_n\text{—O—}$, $Trityl\text{-}(OCH_2CH_2)_n\text{—O—}$.

16. A mixture of liquid crystals containing at least one compound of claim 1.

17. A device comprising two spaced cell walls each bearing electrode structures and treated on at least one facing surface with an alignment layer, a layer of a liquid crystal material enclosed between the cell walls, wherein said device incorporates the liquid crystal material as claimed in claim 16.

* * * * *